United States Patent
Sasaki et al.

(10) Patent No.: US 9,589,103 B2
(45) Date of Patent: Mar. 7, 2017

(54) MEDICAL IMAGE RECORDING/REPRODUCING APPARATUS, MEDICAL IMAGE RECORDING/REPRODUCING METHOD AND COMPUTER READABLE MEDIUM

(75) Inventors: Wataru Sasaki, Kanagawa (JP); Goro Miura, Tokyo (JP); Kunimasa Shimizu, Tokyo (JP); Atsushi Misawa, Saitama (JP); Yasuhiro Asai, Tokyo (JP); Takeshi Misawa, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 416 days.

(21) Appl. No.: 13/296,682

(22) Filed: Nov. 15, 2011

(65) Prior Publication Data
US 2012/0120217 A1    May 17, 2012

(30) Foreign Application Priority Data

Nov. 15, 2010   (JP) .................................. 2010-255381
Nov. 15, 2010   (JP) .................................. 2010-255382

(51) Int. Cl.
H04N 7/18      (2006.01)
G06F 19/00    (2011.01)
A61B 1/00     (2006.01)

(52) U.S. Cl.
CPC .......... *G06F 19/321* (2013.01); *A61B 1/0002* (2013.01); *A61B 1/0005* (2013.01); *A61B 1/00006* (2013.01); *A61B 1/00009* (2013.01)

(58) Field of Classification Search
CPC ............ A61B 1/00006; A61B 1/00009; A61B 1/0005; A61B 1/0002; G06F 19/321
(Continued)

(56) References Cited

U.S. PATENT DOCUMENTS 6,388,702 B1 *   5/2002   Konomura et al. ............ 348/74
2005/0096505 A1 * 5/2005   Imaizumi et al. ............ 600/180
(Continued)

FOREIGN PATENT DOCUMENTS

EP    1 702 556 A1    9/2006
EP    1 790 277 A1    5/2007
(Continued)

OTHER PUBLICATIONS

Extended European Search Report dated Aug. 24, 2012, issued by the European Patent Office in counterpart Application No. 11188962.2.
(Continued)

*Primary Examiner* — Zhihan Zhou
(74) *Attorney, Agent, or Firm* — Sughrue Mion, PLLC

(57) ABSTRACT

A medical image recording apparatus for recording observed images of a subject outputted from a medical instrument, includes: an image arithmetic portion which generates feature images by highlighting specific features contained in the observed images; a display portion which displays inputted display images; a display image switching portion which switches the display images outputted to the display portion to either the observed images or images including the feature images generated by the image arithmetic portion; and an image information recording portion which records, as an image file, image-relevant information including timing information at execution of image switching by the display image switching portion and image generation information for generating the feature images and image information of the observed images.

21 Claims, 14 Drawing Sheets

(58) Field of Classification Search
USPC .......................................................... 348/65
See application file for complete search history.

(56) References Cited

U.S. PATENT DOCUMENTS

| | | |
|---|---|---|
| 2006/0252988 A1 | 11/2006 | Ayame et al. |
| 2006/0253036 A1* | 11/2006 | Takeuchi et al. |
| 2007/0223797 A1* | 9/2007 | Kaneko .......................... 382/128 |
| 2008/0079803 A1* | 4/2008 | Sekiguchi ....................... 348/45 |
| 2009/0252389 A1* | 10/2009 | Yamaguchi ................... 382/128 |
| 2010/0030021 A1* | 2/2010 | Minai et al. .................. 600/109 |
| 2010/0076921 A1 | 3/2010 | Kato et al. |
| 2010/0182413 A1* | 7/2010 | Numata .......................... 348/65 |
| 2010/0195904 A1* | 8/2010 | Tsuruoka ...................... 382/165 |
| 2011/0213203 A1* | 9/2011 | Minai et al. .................. 600/109 |

FOREIGN PATENT DOCUMENTS

| | | |
|---|---|---|
| EP | 1905347 A2 | 4/2008 |
| EP | 1 982 638 A1 | 10/2008 |
| EP | 2138977 A2 | 12/2009 |
| EP | 2149331 A1 | 2/2010 |
| JP | 2005-066057 A | 3/2005 |
| JP | 2006-255323 A | 9/2006 |
| JP | 2006-255324 A | 9/2006 |
| JP | 2006-271871 A | 10/2006 |

OTHER PUBLICATIONS

Office Action dated Oct. 23, 2012, issued by the Japanese Patent Office in counterpart Japanese Patent Application No. 2010-255381.
Office Action dated Oct. 23, 2012, issued by the Japanese Patent Office in counterpart Japanese Patent Application No. 2010-255382.
Office Action dated Apr. 29, 2013 issued by the European Patent Office in counterpart European Patent Application No. 11 188 962.2.
Partial European Search Report issued on Feb. 29, 2012 by the European Patent Office in the counterpart European Patent Application No. 11188962.2.
Search Report dated Nov. 15, 2016 issued by the European Patent Office in counterpart European Patent Application No. 11 188 962.2.

* cited by examiner

MEDICAL IMAGE RECORDING/REPRODUCING APPARATUS, MEDICAL IMAGE RECORDING/REPRODUCING METHOD AND COMPUTER READABLE MEDIUM

CROSS-REFERENCE TO RELATED APPLICATIONS

This application is based on and claims priority under 35 USC 119 from Japanese Patent Application Nos. 2010-255381 filed on Nov. 15, 2010 and 2010-255382 filed on Nov. 15, 2010, the entire content of which is incorporated herein by reference.

1. TECHNICAL FIELD

The present invention relates to a medical image reproducing apparatus, a medical image reproducing method and a program.

2. RELATED ART

Although an inspection result of endoscopic inspection is generally completed as an inspection report with attachments of medical opinions of a doctor giving diagnosis on an inspection region and endoscopic still images, the state of the inspection region and its surrounding affected part may need to be given more detailed observation when, for example, image interpretation about the inspection result is made again after endoscopic inspection. In this case, when motion images are recorded at the time of endoscopic inspection, image interpretation can be made by referring to the recorded motion images. For example, an endoscopic apparatus having a function of recording motion images continuously from the start of inspection in addition to still images has been described in Patent Document 1 (JP-A-2005-66057).

An endoscopic apparatus in which special light diagnosis can be performed in such a manner that an inspection region is irradiated with visible short-wavelength narrow band light so that blood capillary images of a living body tissue surface layer and microscopic patterns of a mucous membrane surface are highlighted has been used recently. In this type endoscopic apparatus, a microscopic structure of a living body tissue which could not be obtained heretofore can be observed by irradiation of an inspection region with visible short-wavelength narrow band light. There is another endoscopic apparatus in which similar special light diagnosis can be performed in such a manner that images observed through an endoscope and obtained not only by irradiation with narrow band light but also by irradiation with white light are subjected to spectroscopic arithmetic processing to form estimated spectroscopic images with an arbitrarily selected wavelength band (e.g. Patent Document 2 (JP-A-2006-255323 corresponding to US2006/0253036) and Patent Document 3 (JP-A-2006-255324 corresponding to US2006/0252988)).

According to each of the aforementioned endoscopic apparatuses, when recorded motion image data is reproduced even after endoscopic inspection, information of the inspection region can be displayed so that image interpretation after the inspection can be performed. However, the recorded motion image data is only ordinary observed images based on white illumination light but a history of observation as to timing in which ordinary observed images were switched to estimated spectroscopic images based on special light diagnosis (diagnosis using estimated spectroscopic images) at the time of endoscopic inspection has not been kept. For this reason, image information observed with image switching by the operator at the time of endoscopic inspection cannot be reproduced after the endoscopic inspection in the same manner as at the time of inspection. What condition of estimated spectroscopic images which was used by the operator to give diagnosis on the effected part when, for example, a focus portion was examined at the time of inspection is unknown.

On the other hand, when a signal outputted to a display portion which displays endoscopic images is recorded as motion image data as it is, both ordinary observed image and estimated spectroscopic image are recorded. However, ordinary images cannot be reproduced from image information recorded as estimated spectroscopic images having limited wavelength components. Moreover, spectroscopic arithmetic processing for obtaining estimated spectroscopic images with a specific wavelength band cannot be performed normally without failure. As a result, it is difficult to give detailed diagnosis on the affected part based on the recorded images at the time of image interpretation after endoscopic inspection.

SUMMARY

An illustrative aspect of the invention to is to provide a medical image reproducing apparatus, a medical image reproducing method and a non-transitory computer readable medium storing a program to execute a process of this method, and a medical image recording apparatus, a medical image recording/reproducing apparatus, a medical image recording method, a medical image recording/reproducing method and a non-transitory computer readable mediums storing a program to execute a process of any one of these method in which image data outputted from a medical instrument can be displayed as the same images as those observed at the time of inspection by means of the medical instrument, and desired feature images can be obtained in accordance with recorded images in any timing.

(1) A medical image reproducing apparatus for reproducing image information recorded as an image file, wherein:

the image file is outputted from a medical instrument capable of switching to either observed images of a subject or images different from the observed images and displaying the switched images, and includes image information of the observed images and timing information indicating display timing of switching to the images different from the observed images and displaying the switched images, the medical image reproducing apparatus includes:

an information extraction portion which extracts the image information and image-relevant information including the timing information from the image file;

an image arithmetic portion which generates feature images by highlighting specific features contained in the observed images by using the extracted image information and the extracted image-relevant information;

a reproducing and display portion which displays inputted display images; and an image switching control portion which switches the display image outputted to the reproducing and display portion to either the recorded image information or the feature images, the image switching control portion having a function of switching the display images in synchronization with the timing information.

(2) A medical image reproducing method for reproducing image information recorded as an image file, wherein:

the image file is outputted from a medical instrument capable of switching to either observed images of a subject or images different from the observed images and displaying the switched images, and includes image information of the observed images and timing information indicating timing of switching to the images different from the observed images and displaying the switched images, the medical image reproducing method includes:

extracting the image information and image-relevant information including the timing information from the image file;

generating feature images by highlighting specific features contained in the observed images by using the extracted image information and the extracted image-relevant information; and switching display images outputted to a reproducing and display portion in synchronization with the timing information when the display images are switched to either the recorded image information or the feature images.

(3) A non-transitory computer readable medium storing a program causing a computer to execute a process for the medical image reproducing method of (2).

(4) A medical image recording apparatus for recording observed images of a subject outputted from a medical instrument, comprising:

an image arithmetic portion which generates feature images by highlighting specific features contained in the observed images;

a display portion which displays inputted display images;

a display image switching portion which switches the display images outputted to the display portion to either the observed images or images including the feature images generated by the image arithmetic portion; and an image information recording portion which records, as an image file, image-relevant information including timing information at execution of image switching by the display image switching portion and image generation information for generating the feature images and image information of the observed images.

(5) A medical image recording/reproducing apparatus includes:

a medical image recording apparatus of (4); and an image reproducing portion which reads an image file recorded by the medical image recording apparatus, and switches to either the observed images or the feature images and displays the switched images on the reproducing and display portion in synchronization with the timing information recorded in the image file.

(6) A medical image recording method for recording observed images of a subject outputted from a medical instrument, includes:

generating feature images by highlighting specific features contained in the observed images; and recording, as an image file, image-relevant information including timing information at execution of image switching and image generation information for generating the feature images and image information of the observed images when display images outputted to a display portion are switched to either the observed images or images including the feature images.

(7) A medical image recording/reproducing method includes:

reading an image file recorded by a medical image recording method of (6); and switching to either the observed images or the feature images and displaying the switched images on the reproducing and display portion in synchronization with the timing information recorded in the image file.

(8) A non-transitory computer readable medium stores a program causing a computer to execute a process for the medical image recording method of (6).

(9) A non-transitory computer readable medium stores a program causing a computer to execute a process for the medical image recording method of (7).

According to the invention, image data of motion images outputted from a medical instrument can be displayed as the same images as those observed at the time of inspection by means of the medical instrument, and desired feature images can be obtained in accordance with recorded images in any timing.

DETAILED DESCRIPTION

An exemplary embodiment of the invention will be described below in detail with reference to the drawings.

In this specification, the case where a medical image recording apparatus or a medical image recording/reproducing apparatus records/reproduces endoscopic images will be described illustratively. That is, an image recording apparatus records, as an image file, motion image information of observed images of a subject captured at the time of endoscopic inspection and timing information indicating timing of display switching to specific feature images corresponding to the observed images. As a result, when an image reproducing apparatus reads the recorded image file and reproduces the image information based on the image file, the images observed at the time of endoscopic inspection can be reproduced as motion images having the same contents as observed. The image recording apparatus records image information so that an arbitrary spectroscopic arithmetic operation can be applied on the image reproducing apparatus side normally at any timing.

Figure 1:
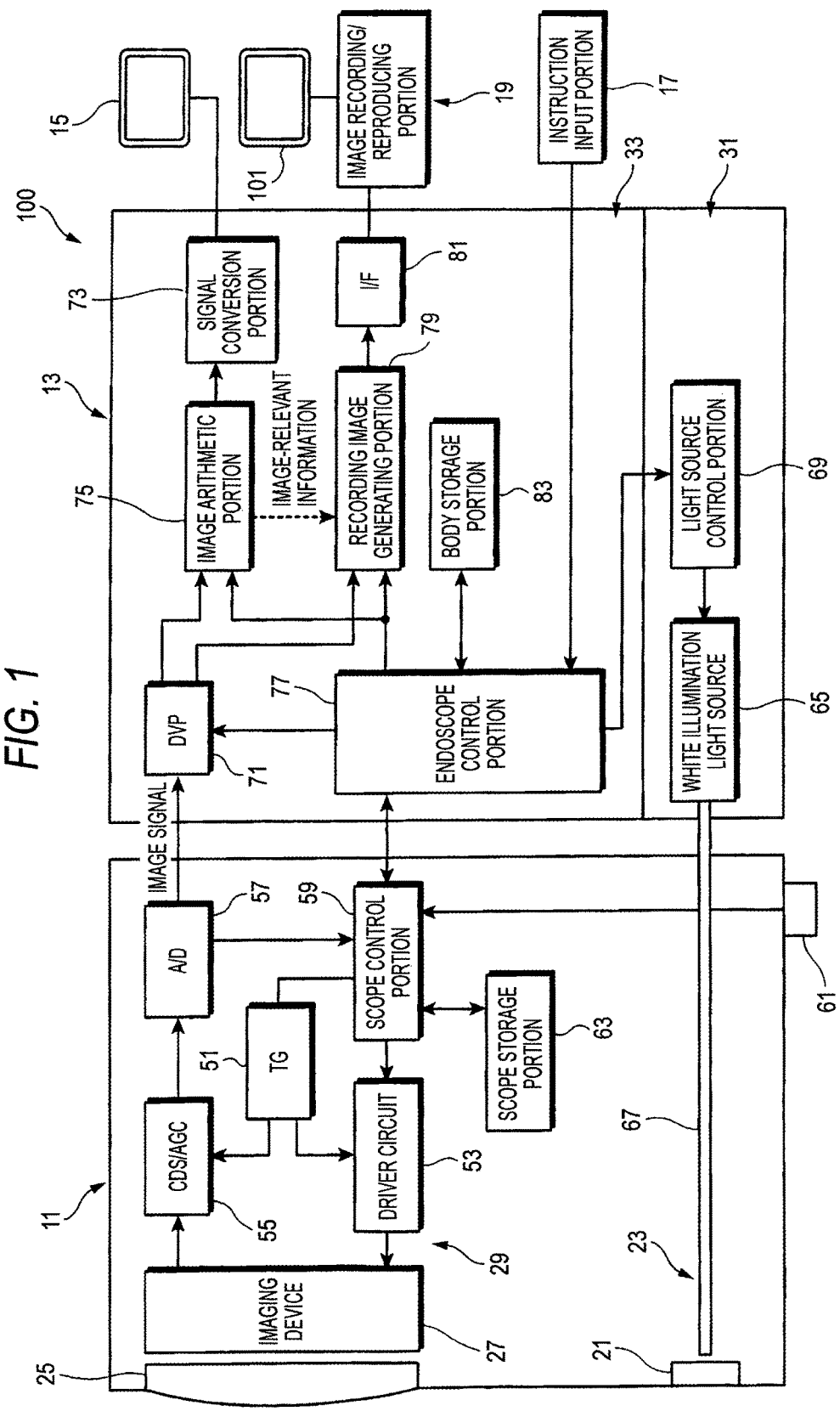
FIG. 1 is a block diagram of configuration of an endoscope-including medical image recording apparatus for explaining an exemplary embodiment of the invention.
Figure 2:
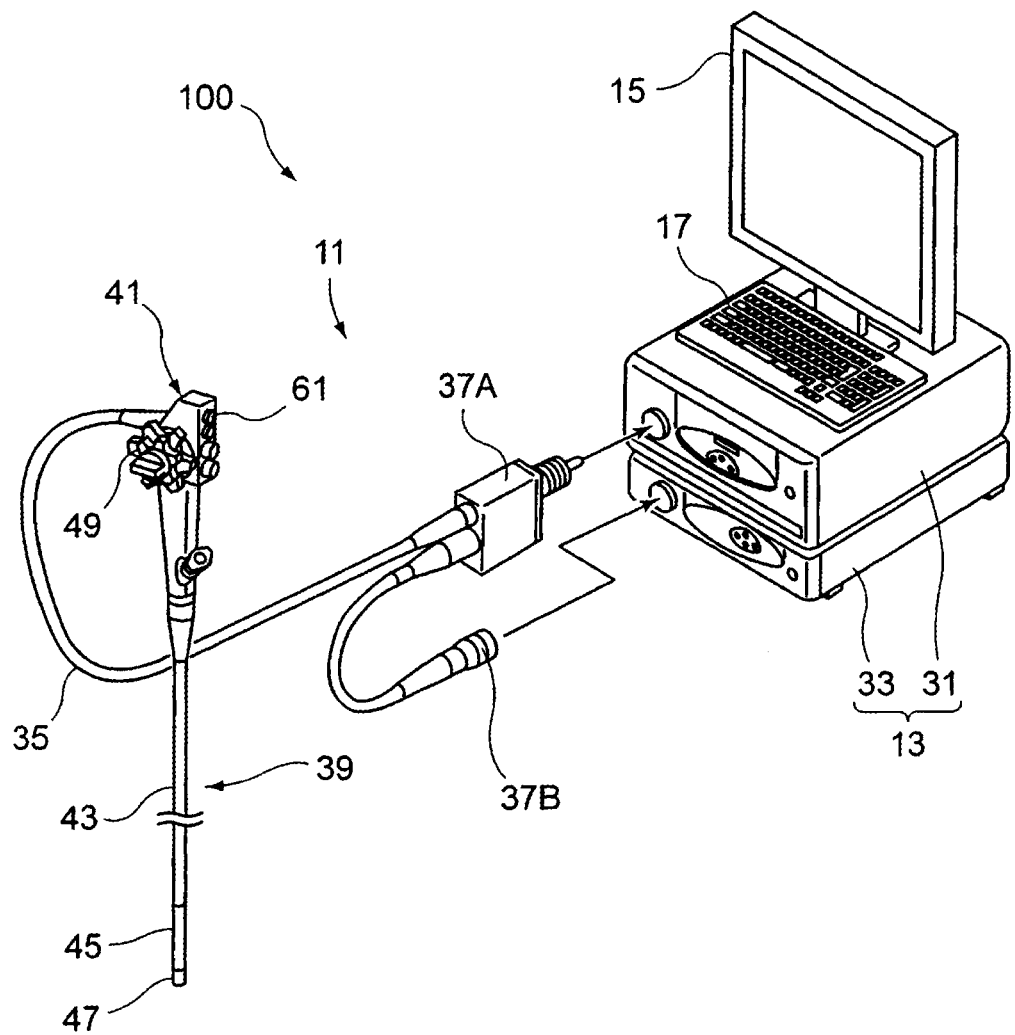
FIG. 2 is an external view showing an example of the endoscope.

FIG. 1 is a block diagram of configuration of an endoscope-including medical image recording apparatus for explaining an exemplary embodiment of the invention. FIG. 2 is an external view showing an example of an endoscope.

As shown in FIGS. 1 and 2, the medical image recording apparatus 100 connected to the endoscope 11 has an endoscope controller 13, a display portion 15 for displaying inputted display images, an instruction input portion 17 for receiving an instruction given to the endoscope controller 13, and an image recording/reproducing portion 19 connected to the endoscope controller 13 and provided for recording endoscopic images.

The endoscope 11 is an electronic endoscope which has an illumination optical system 23 and an imaging optical system 29. The illumination optical system 23 has an illumination window 21 for irradiating a subject with illumination light. The imaging optical system 29 has an observation window 25 for observing the subject, and an imaging device 27.

The endoscope controller 13 has a light source portion 31 for supplying illumination light to the illumination optical system 23 of the endoscope 11, and a processor 33 for applying signal processing to an image signal outputted from the imaging optical system 29. The endoscope 11 is removably attached to the endoscope controller 13 through universal cords 35 and connectors 37A and 37B shown in FIG. 2.

As shown in FIG. 2, the endoscope 11 has an endoscope insertion portion 39, an endoscope manipulation portion 41 which performs manipulation to curve a front end of the endoscope insertion portion or performs manipulation for observation, and the universal cords 35 and the connectors 37A and 37B through which the endoscope 11 is connected to the endoscope controller 13.

The endoscope insertion portion 39 is configured so that a soft portion 43 having flexibility, a curvable portion 45 and a front end portion (hereinafter also referred to as endoscope front end portion) 47 are formed in this order toward the front end. The illumination window 21 of the illumination optical system 23 and the observation window 25 of the imaging optical system 29 shown in FIG. 1 are disposed in the endoscope front end portion 47. The imaging device 27 is disposed inside the observation window 25 through an objective lens unit (not shown).

The curvable portion 45 can be curved freely by a rotating operation of an angle knob 49 disposed in the endoscope manipulation portion 41 shown in FIG. 2. The curvable portion 45 can be curved in any direction at any angle in accordance with a region of the subject in which the endoscope 11 is used, so that the illumination window 21 and the observation window 25 in the endoscope front end portion 47 can be directed toward a desired observation region.

The imaging optical system 29 has the imaging device 27 such as a CCD (Charge Coupled Device) type image sensor or a CMOS (Complementary Metal-Oxide Semiconductor) type image sensor. A color image signal having intensity information of basic color components including blue (B), green (G) and red (R) is outputted from the imaging device 27.

A driver circuit 53 which forms driving pulses based on a sync signal outputted from a timing generator (TG) 51 is connected to the imaging device 27. A CDS/AGC (Correlated Double Sampling/Automatic Gain Control) circuit 55 which samples and amplifies a signal (image signal) outputted from the imaging device 27 is connected to the imaging device 27. An A/D converter 57 is provided in the rear of the CDS/AGC circuit 55. An analog image signal outputted from the CDS/AGC circuit 55 is converted into a digital image signal by the A/D converter 57.

Incidentally, the imaging device 27 may be a primary color type imaging device which outputs RGB signals or may be a complementary color type imaging device including cyan (C), magenta (M), yellow (Y) (and green (G)). When the imaging device 27 is a complementary color type imaging device, a color conversion circuit which converts a complementary color system into a primary color system may be provided in a signal processing circuit.

According to the configuration of the imaging optical system, when an image of the subject illuminated through the illumination window 21 is captured by the imaging device 27, an imaging signal of the subject is outputted from the imaging device 27 driven by the driver circuit 53. The imaging signal is amplified by the CDS/AGC circuit 55 in a correlated double sampling and automatic gain control manner and then fed as an image signal of a digital signal to a DPV 71 of the processor 33 through the A/D converter 57.

A scope control portion 59 controls various circuits of the imaging optical system 29. Signals from various operation buttons 61 disposed in the endoscope manipulation portion 41 shown in FIG. 2 and including an observation mode change button which will be described later in detail are inputted to the scope control portion 59. A scope storage portion 63 is connected to the scope control portion 59 so that the scope control portion 59 can perform processing based on various kinds of information stored in the scope storage portion 63 in advance.

The illumination optical system 23 guides light emitted from a white illumination light source 65 of the light source portion 31 to the illumination window 21 of the endoscope 11 through a fiber bundle 67 so that a light source control portion 69 controls the quantity of light of the white illumination light source 65.

The processor 33 is provided with the DVP (Digital Video Processor) 71 which applies various kinds of image processing to the digitized image signal. The DVP 71 normalizes R, G and B image information based on the image signal from the imaging device 27 and then performs noise removal, white balance processing, etc. to thereby form and output an ordinary image which is an observed image based on white illumination light.

The processor 33 inputs information of the ordinary image as the white illumination light-based observed image formed and outputted by the DVP 71 to a signal conversion portion 73 through an image arithmetic portion 75 which will be described later in detail, so that the information of the ordinary image is converted into a Y/C signal format composed of a luminance (Y) signal and a color difference [C(R-Y, B-Y)] signal by the signal conversion portion 73. As a result, the resulting information is outputted as image information to be displayed on the display portion 15.

Upon reception of a control signal from an endoscope control portion 77, the image arithmetic portion 75 performs switching to one of the case where the ordinary image information inputted from the DVP 71 is directly outputted to the signal conversion portion 73 as described above and the case where the ordinary image information is subjected to spectroscopic arithmetic processing and then outputted to the signal conversion portion 73. A feature image which is an estimated spectroscopic image when the ordinary image information is subjected to spectroscopic arithmetic processing is switched to the ordinary image so that the switched ordinary image is displayed on the display portion 15.

The DVP 71 further outputs the ordinary image information to a recording image generating portion 79. Upon reception of a control signal from the endoscope control portion 77, the recording image generating portion (image information recording portion) 79 generates recording image (motion image) data to be recorded as an image file, and outputs the recording image (motion image) data to the image recording/reproducing portion 19 through an interface 81. The image data as the observed image recorded by the recording image generating portion 79 is image data which has been already subjected to a general normalization process such as white balance processing but has not been subjected to a specific feature highlighting process yet.

The endoscope control portion 77 is connected to a body storage portion 83. The endoscope control portion 77 performs various kinds of control such as display, recording, etc. of endoscopic images based on various kinds of information and programs stored in the body storage portion 83 in advance. The endoscope control portion 77 is further connected to the scope control portion 59 of the endoscope 11 so that the endoscope control portion 77 can perform control in synchronization with the endoscope 11 side.

Figure 3:
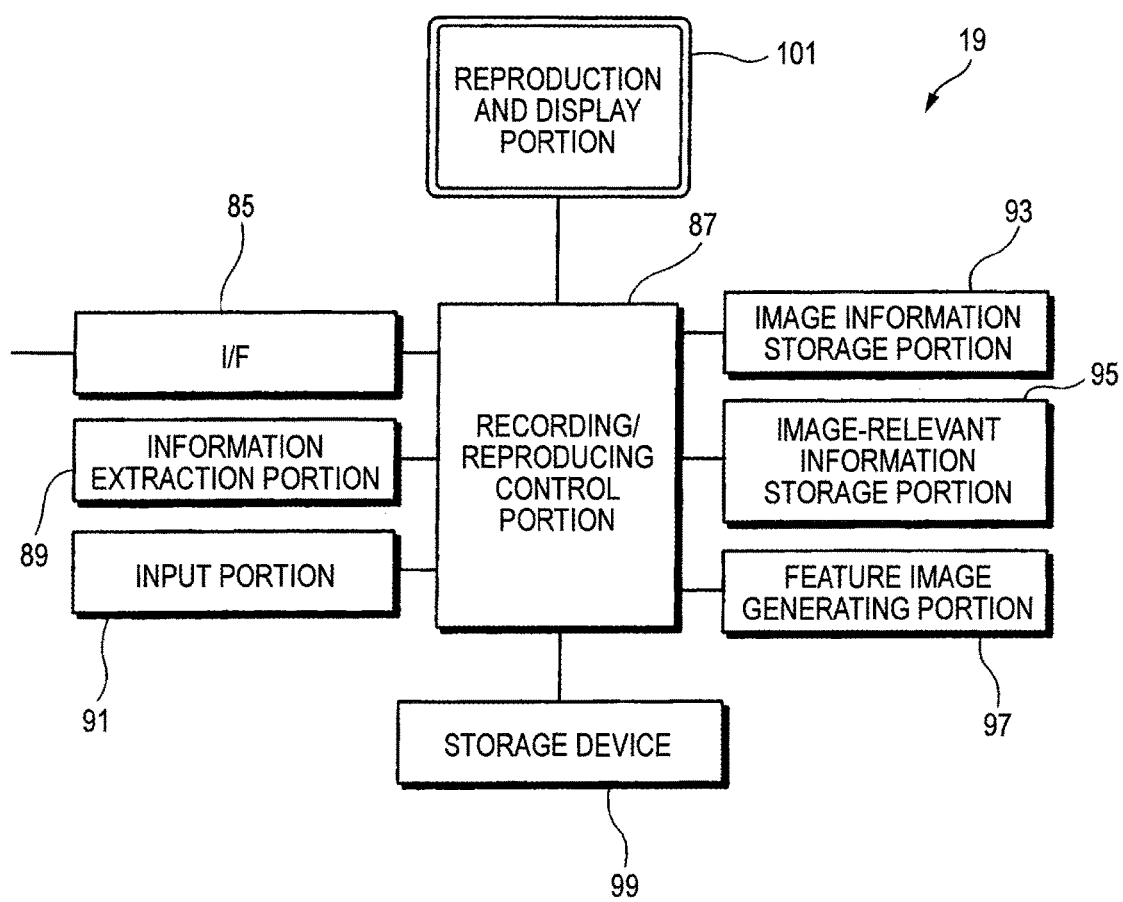
FIG. 3 is a block diagram of configuration of an image recording/reproducing portion.

FIG. 3 is a block diagram of configuration of the image recording/reproducing portion 19.

The image recording/reproducing portion 19 has a recording/reproducing control portion 87, an information extraction portion 89, an input portion 91, an image information storage portion 93, an image-relevant information storage portion 95, a feature image generating portion 97, a storage device 99, and a reproducing and display portion 101. Recording image data outputted from the recording image generating portion 79 (see FIG. 1) is inputted to the recording/reproducing control portion 87 through an interface 85. The information extraction portion 89, the input portion 91, the image information storage portion 93, the image-relevant information storage portion 95, the feature image generating portion 97, the storage device 99, and the reproducing and display portion 101 are connected to the recording/reproducing control portion 87.

The image recording/reproducing portion 19 alone may function also as a medical image reproducing apparatus which reproduces an image file generated by the medical image recording apparatus 100. The whole of the medical image recording apparatus 100 including the image recording/reproducing portion 19 functions as a medical image recording/reproducing apparatus.

The recording/reproducing control portion 87 records image data generated by the recording image generating portion 79 as an image file in the storage device 99. The storage device 99 may be configured so as to be provided in the image recording/reproducing portion 19 or may be configured so as to be connected to the endoscope controller 13 directly or through a network.

When the image recording/reproducing portion 19 reads and reproduces a recorded image file, the information extraction portion 89 analyzes the image file recorded in the storage device 99 and extracts observed image-including recording image information and image-relevant information concerned with the observed image. The recording/reproducing control portion 87 controls the image information storage portion 93 to store the extracted recording image information and controls the image-relevant information storage portion 95 to store the image-relevant information.

The feature image generating portion 97 generates a feature image obtained by highlighting specific features contained in the observed image by using the observed image stored in the image information storage portion 93 and the image-relevant information stored in the image-relevant information storage portion 95. The input portion 91 inputs the contents and type of the image to be displayed on the reproducing and display portion 101 to the recording/reproducing control portion 87.

<Recording of Endoscopic Observed Image as Image File>

A process in which the medical image recording apparatus 100 configured as described above records, as an image file, motion image information of observed images obtained by capturing images of a subject at the time of endoscopic inspection and timing information indicating timing of display switching to specific feature images corresponding to the observed images will be described below.

Figure 4:
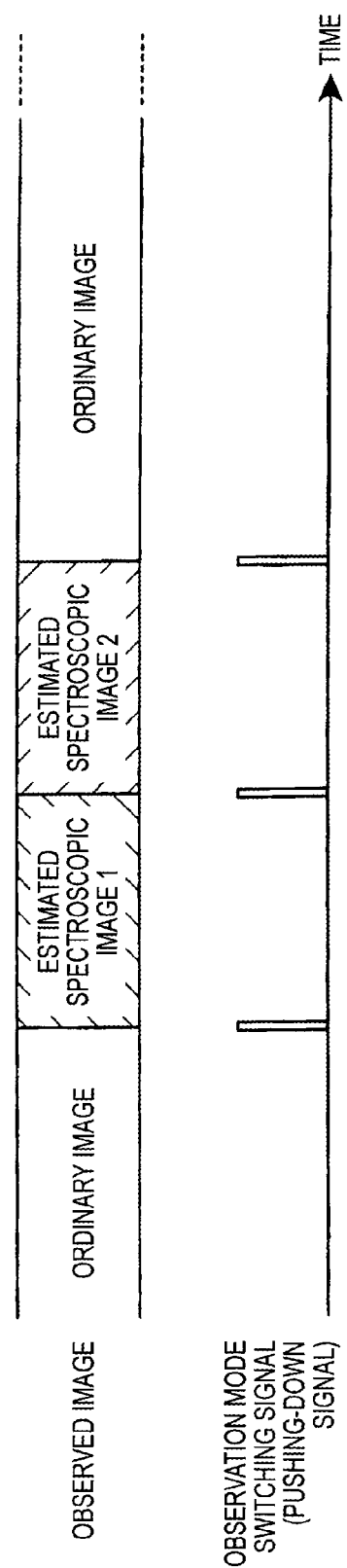
FIG. 4 is a time chart of an observed image and a switching signal in the case where observed image switching is executed by an endoscope operator.

FIG. 4 shows a time chart of an observed image and a switching signal when an endoscopic operator performs switching of the observed image.

When the endoscopic operator inserts the endoscope insertion portion 39 of the endoscope 11 shown in FIG. 2 into a body cavity of a patient and conducts diagnosis on an inspection region in the body cavity, an image signal from the imaging device 27 of the endoscope 11 shown in FIG. 1 is inputted to the DVP 71 of the processor 33 so that information of an ordinary image which is an observed image based on white illumination light is displayed on the display portion 15 through the image arithmetic portion 75 and the signal conversion portion 73.

When the operator pushes down any one of the observation mode change buttons 61 of the endoscope manipulation portion 41 (see FIG. 2) to change the observation mode from an ordinary observation mode to a spectroscopic image observation mode for special light diagnosis, the image arithmetic portion 75 performs spectroscopic arithmetic processing so that the image displayed on the display portion 15 changes from an ordinary image to an estimated spectroscopic image 1. Moreover, whenever the observation mode change button 61 is pushed down, the arithmetic operation condition in the image arithmetic portion 75 is changed so that the image displayed on the display portion 15 changes from the estimated spectroscopic image 1 to an estimated spectroscopic image 2 and from the estimated spectroscopic image 2 to the ordinary image.

Switching of the displayed image is performed in such a manner that whenever the endoscope control portion 77 of the processor 33 receives the observation mode change button 61 pushing-down signal outputted from the scope control portion 59, the endoscope control portion 77 of the processor 33 outputs a switching signal to the image arithmetic portion 75 so that the image arithmetic portion 75 changes the contents of the spectroscopic arithmetic processing. That is, the image arithmetic portion 75 changes the spectroscopic arithmetic operation condition based on the control signal outputted from the endoscope control portion 77 in accordance with pushing-down of the observation mode change button 61 to generate different kinds of estimated spectroscopic images 1, 2, . . . and ordinary images not subjected to the spectroscopic arithmetic processing. That is, the image arithmetic portion 75 functions as a display image switching portion which switches the displayed image in synchronization with the observation mode change button 61 pushing-down signal.

<Generation of Estimated Spectroscopic Images>

Figure 5:
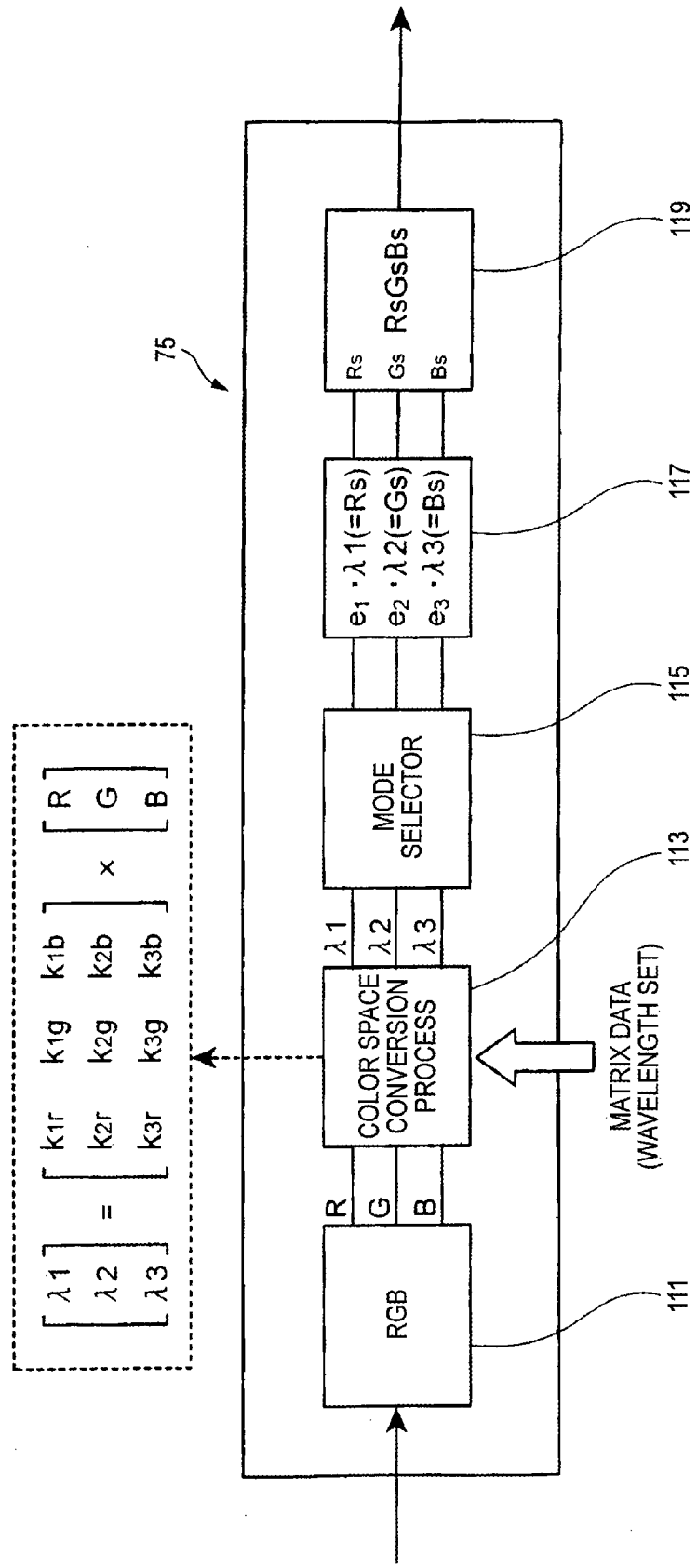
FIG. 5 is a detailed block diagram of configuration of an image arithmetic portion.

A procedure in which estimated spectroscopic images are generated by the image arithmetic portion 75 will be described below. FIG. 5 is a detailed block diagram showing configuration of the image arithmetic portion 75. The image arithmetic portion 75 has a first color conversion circuit 111, and a color space conversion processing circuit 113. The first color conversion circuit 111 decomposes an inputted image signal into RGB signals and outputs the RGB signals. The color space conversion processing circuit 113 applies a matrix arithmetic operation for estimated spectroscopic images to the RGB signals. The color space conversion processing circuit 113 outputs estimated spectroscopic image signals with selected wavelengths λ1, λ2 and λ3 (referred to as a wavelength set). Estimated spectroscopic images are images obtained by matrix arithmetic operation of estimated spectroscopic images with wavelengths arbitrarily set in accordance with target images (observed images).

Matrix data (one table) stored in the body storage portion 83 or the scope storage portion 63 (see FIG. 1) so as to be used for the matrix arithmetic operation in the color space conversion processing circuit 113 is shown in the following Table 1.

TABLE 1

| parameter | $k_{pr}$ | $k_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −3.6E−05 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |

For example, the matrix data shown in Table 1 is composed of 61 wavelength band parameters p1 to p61 obtained by separating a wavelength range of from 400 nm to 700 nm at intervals of 5 nm. Each of the parameters p1 to p61 is composed of coefficients kpr, kpg and kpb (p is equivalent to one of p1 to p61) for the matrix arithmetic operation. Incidentally, the wavelength band parameters are stored in the body storage portion 83 of the endoscope controller 13 or the scope storage portion 63 so that the wavelength band parameters can be referred to at any time.

In the color space conversion processing circuit 113, a matrix arithmetic operation represented by the following expression 1 is performed based on the coefficients kpr, kpg and kpb and the RGB signals outputted from the first color conversion circuit 111.

$$\begin{bmatrix} \lambda 1 \\ \lambda 2 \\ \lambda 3 \end{bmatrix} = \begin{bmatrix} k1r & k1g & k1b \\ k2r & k2g & k2b \\ k3r & k3g & k3b \end{bmatrix} \times \begin{bmatrix} R \\ G \\ B \end{bmatrix} \quad \text{[Numeral 1]}$$

That is, when, for example, parameters p21 (center wavelength 500 nm), p45 (center wavelength 620 nm) and p51 (center wavelength 650 nm) in Table 1 are selected in the condition that the wavelength set is set to include λ1, λ2 and λ3, (−0.00119, 0.002346, 0.0016) in p21, (0.004022, 0.000068, −0.00097) in p45 and (0.005152, −0.00192, 0.000088) in p51 can be assigned as the coefficients (kpr, kpg, kpb).

The color space conversion processing circuit 113 is provided with a mode selector 115 which selects one of a spectroscopic image (monochrome mode) with one wavelength band (narrow band) and a spectroscopic image (trichrome mode) with three wavelength bands. An amplification circuit 117 is connected to follow the mode selector 115. The amplification circuit 117 amplifies λ1, λ2 and λ3 signals for forming estimated spectroscopic images with gain values $e_1$, $e_2$ and $e_3$ respectively and outputs amplified signals $e_1 \times \lambda 1$, $e_2 \times \lambda 2$ and $e_3 \times \lambda 3$. The amplification circuit 117 is provided with a second color conversion circuit 119 into which the amplified λ1, λ2 and λ3 signals are inputted as Rs, Gs and Bs signals in order to be subjected to processing corresponding to the conventional RGB signals.

Incidentally, the DVP 71 may form not RGB signals but Y/C signals composed of a luminance (Y) signal and color difference (R-Y, B-Y) signals. In this case, the image arithmetic portion 75 converts the Y/C signals into RGB signals before the aforementioned matrix arithmetic operation is performed.

<Example of Motion Image Recording Control>

Figure 6:
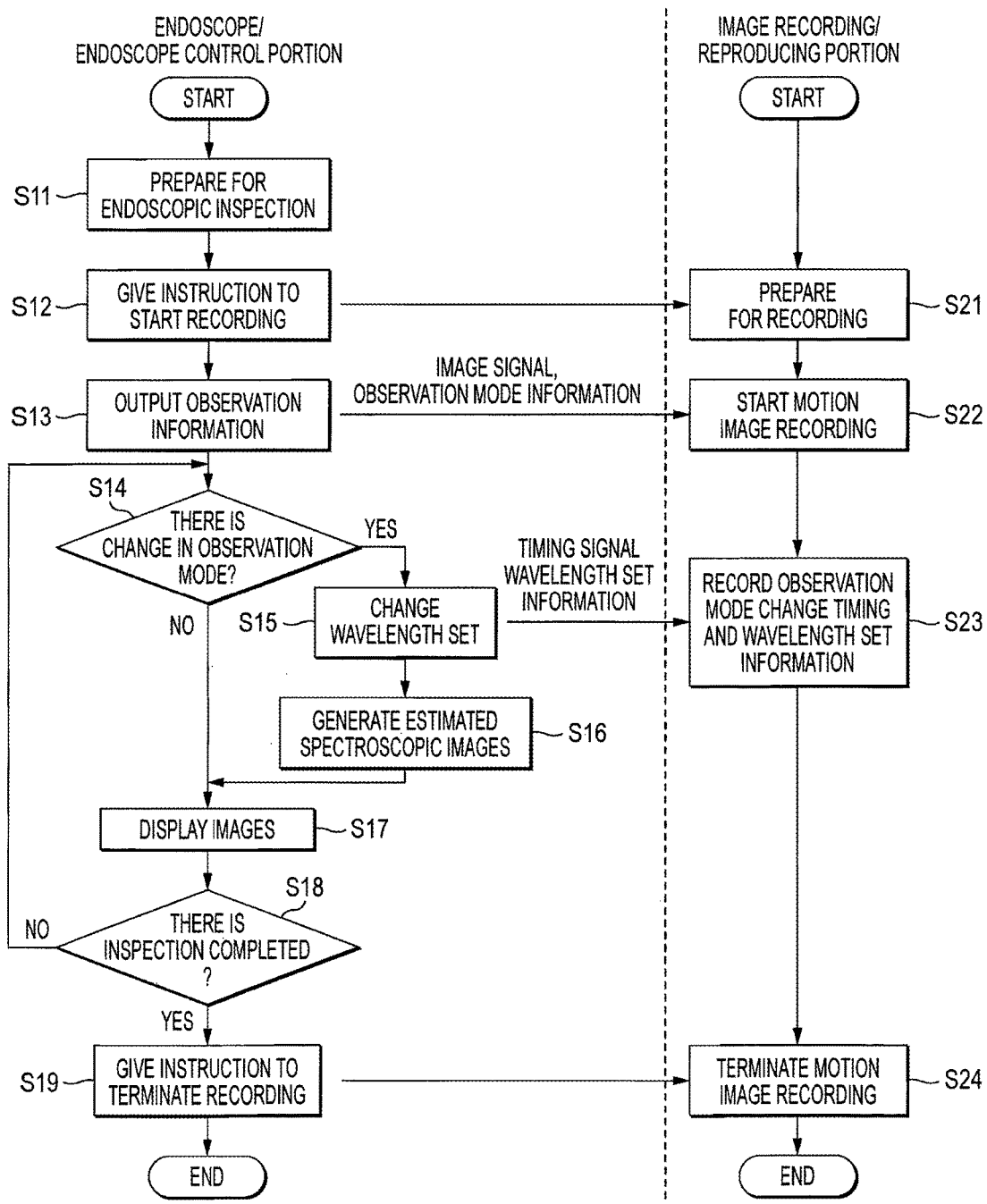
FIG. 6 is an explanatory view showing a flow chart showing a procedure of recording observed images as an image file and a state of information transmission between the observation side where an endoscope and an endoscope controller are provided and the image recording side where an image recording/reproducing portion is provided.

A procedure in which observed images for endoscopic inspection are recorded as an image file of motion images will be described below. FIG. 6 shows a flow chart showing a procedure of recording observed images as an image file and a state of information transmission between the observation side where the endoscope 11 and the endoscope control portion 13 are provided and the image recording side where the image recording/reproducing portion 19 is provided.

First, the medical image recording apparatus 100 including the endoscope 11 is powered on to prepare for endoscopic inspection (S11). Just before or just after the endoscope 11 is inserted into the body cavity of a patient as a subject, the operator gives an instruction to start recording, for example, by an operation of pushing down any one of the operation buttons 61. A recording start instruction signal on this occasion is sent to the image recording/reproducing portion 19 through the scope control portion 59 and the endoscope control portion 77 (S12). Upon reception of the recording start instruction signal, the image recording/reproducing portion 19 makes preparations for recording (S21).

After the recording start instruction is issued from the endoscope 11, the endoscope control portion 77 outputs the output image signal of the endoscope 11 from the DVP 71 to the recording image generating portion 79, reads the current observation mode (an ordinary observation mode, an estimated spectroscopic image observation mode, etc.) of the endoscope 11 from the scope control portion 59 and outputs information of the current observation mode to the recording image generating portion 79. The recording image generating portion 79 generates recording image information based on the image signal and the observation mode information and outputs the recording image information to the image recording/reproducing portion 19 (S13).

The image recording/reproducing portion 19 starts to record the received recording image information as an image file on the storage device 99 (FIG. 3) (S22). As a result, motion image recording of observed images of the endoscope 11 by the image recording/reproducing portion 19 is started.

When the operator performs an operation of pushing down any one of the operation buttons 61 to change the observation mode (S14), the endoscope control portion 77 switches the image information outputted to the display portion 15 to ordinary image, estimated spectroscopic image 1, estimated spectroscopic image 2, . . . in accordance with each pushing-down operation as described above with reference to FIG. 4. That is, estimated spectroscopic images outputted from the image arithmetic portion 75 or ordinary images outputted as they are from the DVP 71 are selectively inputted to the signal conversion portion 73 which outputs image information to the display portion 15, so that the contents displayed on the display portion 15 are changed.

On the other hand, the recording image generating portion 79 receives ordinary images outputted from the DVP 71 and receives timing information at change of the observation mode and wavelength set ($\lambda 1$, $\lambda 2$ and $\lambda 3$) information which is image generation information for generating estimated spectroscopic images. The timing information and the designated wavelength set information are inputted from the scope control portion 59 to the recording image generating portion 79 through the endoscope control portion 77.

That is, when the operator changes the observation mode, the endoscope control portion 77 changes the wavelength set used for spectroscopic arithmetic processing by the image arithmetic portion 75 (S15) and outputs a timing signal indicating timing of changing the observation mode and changed wavelength set information to the recording image generating portion 79. The recording image generating portion 79 collects and outputs these kinds of information to the image recording/reproducing portion 19. The image recording/reproducing portion 19 records the inputted information as an image file in synchronization with observed image information (S23).

When the estimated spectroscopic image observation mode is selected, the image arithmetic portion 75 generates estimated spectroscopic images corresponding to the changed wavelength set (S16) and outputs the estimated spectroscopic images to the display portion 15 (S17). In this case, the image arithmetic portion 75 generates estimated spectroscopic images based on respective information of the ordinary images outputted from the DVP 71, the matrix data stored in the body storage portion 83 (or the scope storage portion 63) and the set wavelength set.

The endoscope control portion 77 outputs either ordinary images based on the image signal given from the imaging device 27 or estimated spectroscopic images generated as described above to the signal conversion portion 73 so that the images are displayed on the display portion 15 (S17).

The steps S14 to S18 are repeated until the endoscopic inspection is completed (S18). When the inspection is completed, the endoscope control portion 77 outputs a recording termination instruction signal to the image recording/reproducing portion 19 (S19). Then, the image recording/reproducing portion 19 terminates motion image recording and stores an image file in the storage device 99 (S24).

<Image File Format>

The format of the image file recorded in the storage device 99 by the image recording/reproducing portion 19 will be described below.

A general-purpose image file format such as a motion JPEG format can be used as the format of the image file in which the motion images are recorded. The motion JPEG format is a compression/recording format which applies JPEG as an image compression format to generation of motion image data and in which compressed JPEG images are arranged as respective frames so that motion images are reproduced. The motion JPEG is the same as a motion JPEG2000 format defined in the standard specification.

Figure 7:
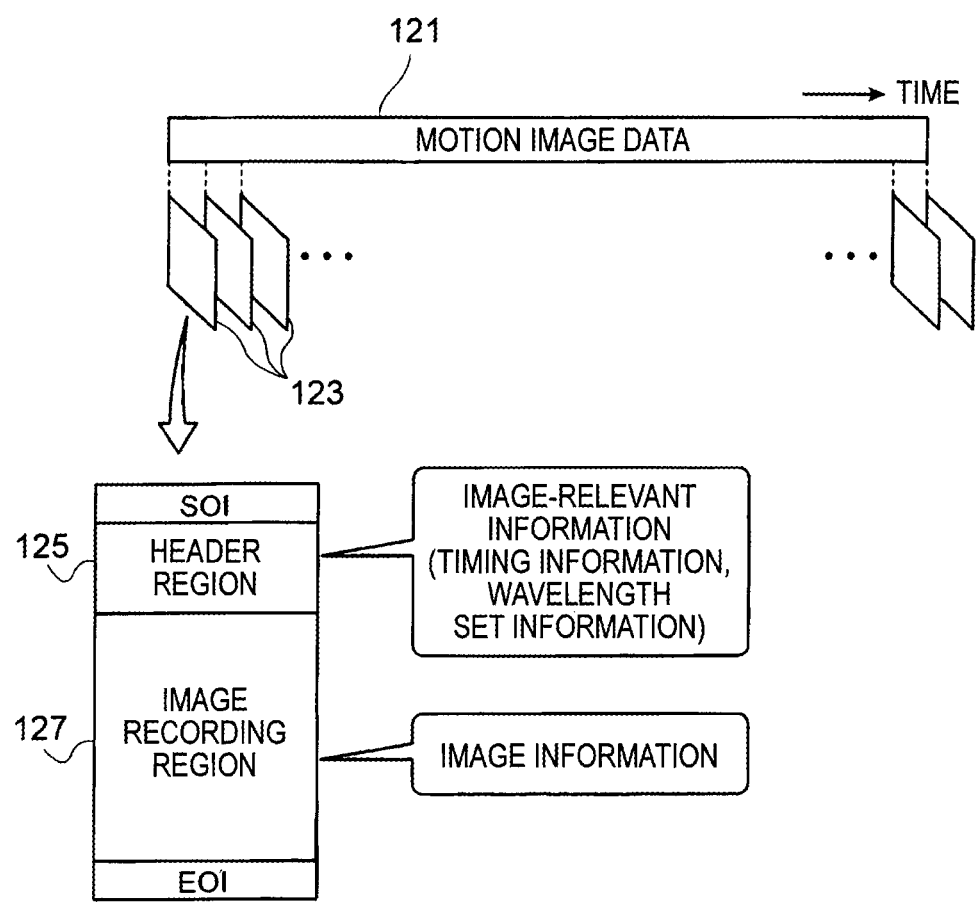
FIG. 7 is an explanatory view schematically showing the configuration of an image file.

FIG. 7 is an explanatory view schematically showing the configuration of the image file. The image file recorded in the storage device 99 by the image recording/reproducing portion 19 (see FIG. 3) is motion image data 121 on which observed images from the start to the end of the endoscopic inspection are recoded and which is composed of a large number of JPEG images 123. Each JPEG image is composed of segments so that a header region 125 and an image recording region 127 are provided between SOI (Start Of Image) and EOI (End Of Image).

Timing information at execution of image switching and wavelength set information are recorded in the header region 125 of each JPEG image 123. Image information of an observed image is recorded in the image recording region 127. That is, timing information at execution of image switching, image-relevant information including image generation information for generating estimated spectroscopic images, and information of observed images are recorded as one image file. As a result, data input/output can be performed at a high speed and it is easy to manage the image file.

The information of observed images is fed continuously from the image signal outputted from the endoscope 11. The timing information and wavelength set information included in the image-relevant information are set in accordance with operation of the operation buttons 61 of the endoscope 11, the instruction input portion 17, etc. shown in FIG. 1 or by direct inputting. The wavelength set information is set to have a default value for display of an initial (first) estimated spectroscopic image.

Besides the motion JPEG format, a commonly known format such as an MPEG-4 AVC format, an H.264 format, etc. can be used as the image file format.

<Procedure of Reproduction of Recorded Image File>

Referring again to FIG. 3 which is a block diagram of the configuration of the image recording/reproducing portion 19, a basic procedure for reading an image file recorded as described above and reproducing recorded images of the image file will be described below. The medical image recording apparatus 100 provided with the image recording/reproducing portion 19 can perform both image recording and reproduction.

The recording/reproducing control portion 87 reads an image file from the storage device 99 and sends the image file to the information extraction portion 89. The information extraction portion 89 extracts recording image information including observed images and image-relevant information including timing information at execution of image switching and wavelength set information for generating estimated spectroscopic images.

The recording/reproducing control portion 87 controls the image information storage portion 93 to store the extracted recording image information and controls the image-relevant information storage portion 95 to store the image-relevant information. The feature image generating portion 97 generates feature images as estimated spectroscopic images observed at the time of endoscopic inspection, based on these kinds of information.

The feature image generating portion 97 has a function of selectively generating observed images (ordinary images and estimated spectroscopic images) at the time of endoscopic inspection, estimated spectroscopic images obtained by arithmetic processing based on a prepared wavelength set or estimated spectroscopic images obtained by arithmetic processing based on any input wavelength set. That is, the image recording/reproducing portion 19 can select any one from various prepared image reproduction modes.

Figure 8:
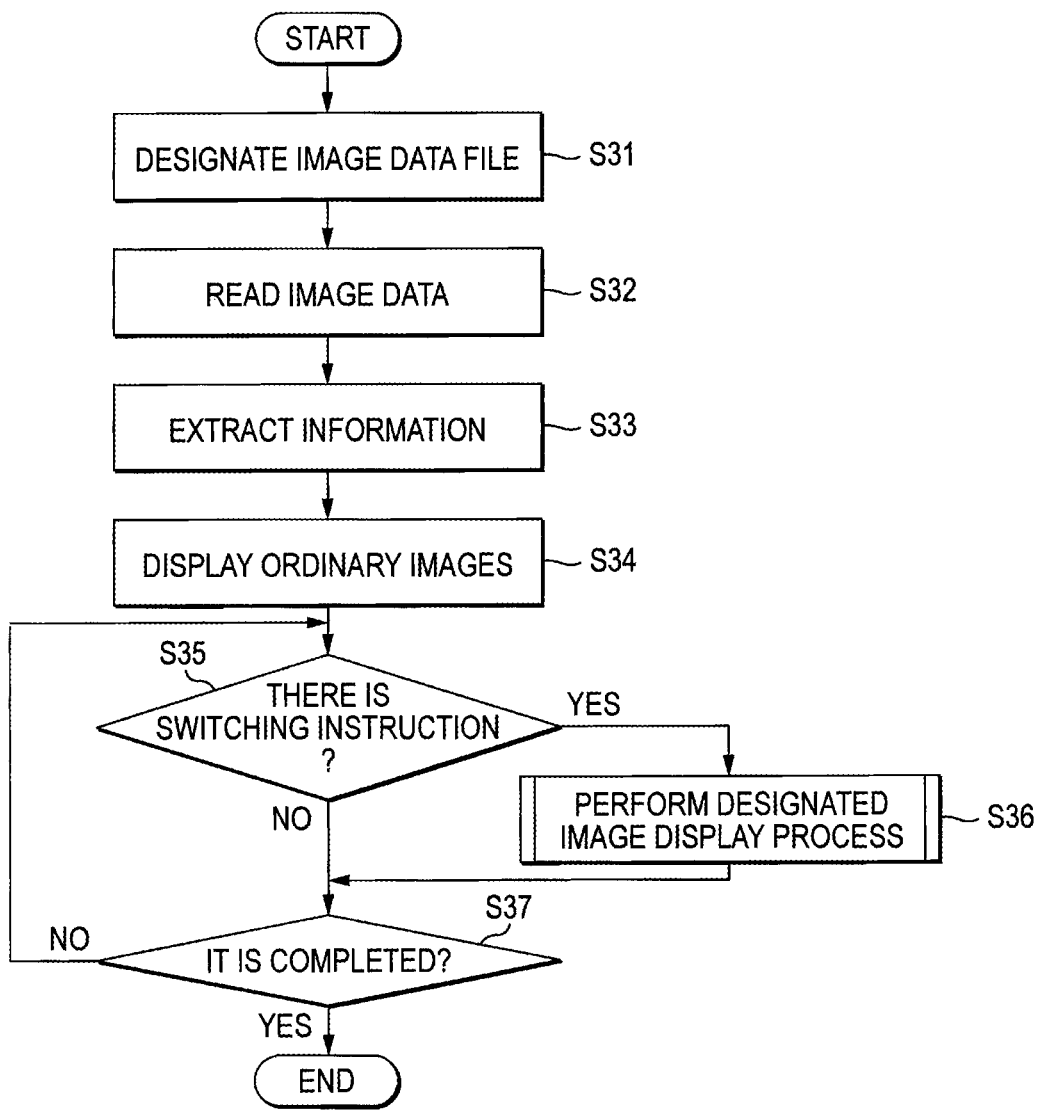
FIG. 8 is a flow chart showing a specific procedure of reproducing an image file by the image recording/reproducing portion.

Here, a specific procedure in which an image file is reproduced by the image recording/reproducing portion 19 will be described with reference to a flow chart shown in FIG. 8.

First, the recording/reproducing control portion 87 controls the reproducing and display portion 101 to display a large number of image files recorded on the storage device 99. The operator designates an image file to be reproduced through the input portion 91 while viewing the reproducing and display portion 101 (S31).

The recording/reproducing control portion 87 reads the image file designated through the input portion 91 from the storage device 99 (S32) and controls the information extraction portion 89 to analyze the image file format and extract respective recorded information. Of the respective extracted information, recording image information is outputted to the image information storage portion 93 and timing information at execution of image switching and wavelength set information for generating estimated spectroscopic images are outputted to the image-relevant information storage portion (S33). On this occasion, the information extraction portion 89 expands recoded images compressed as JPEG images and converts the images into RGB image signals.

The recording/reproducing control portion 87 controls the reproducing and display portion 101 to reproduce and display ordinary images stored in the image information storage portion 93. As a result, the ordinary images are reproduced and displayed (S34).

Figure 9:
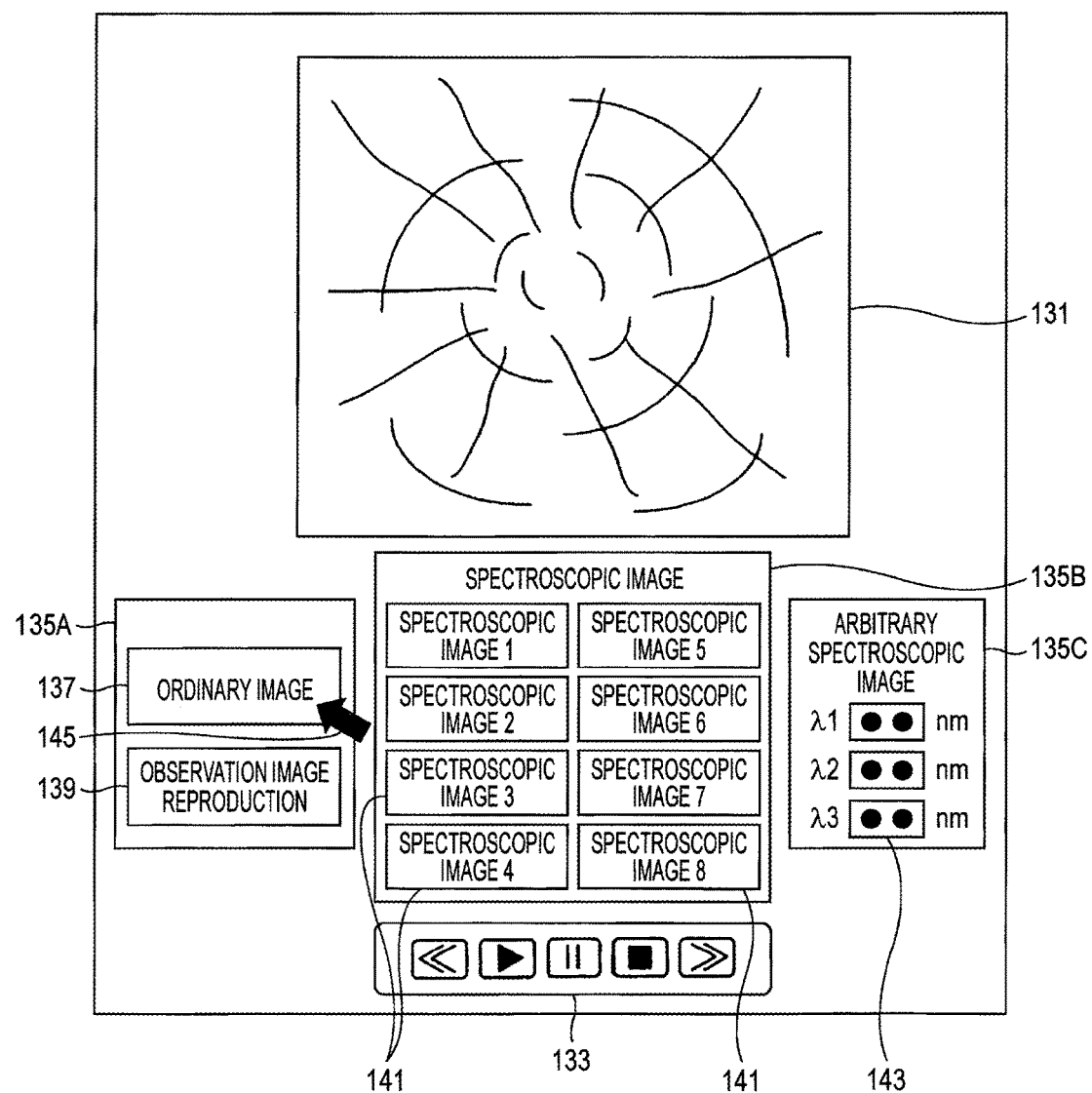
FIG. 9 is an explanatory view showing an example of reproduction and display.

FIG. 9 shows an example of display on the reproducing and display portion 101 on this occasion. Image information 131 recorded on the image file is displayed on the reproducing and display portion 101. A playback operation region 133 for performing playback operation such as play, stop, forward feed, rewind, etc. of image information and image selection regions 135A, 135B and 135C for selecting the kind of image information to be displayed are arranged in a display screen of the reproducing and display portion 101.

An ordinary image button 137 for displaying ordinary images as observed images recorded as an image file at the time of endoscopic inspection and an observation image playback button 139 for reproducing images in the same manner as image switching was executed at the time of endoscopic inspection are arranged in the image selection region 135A. Wavelength set selection buttons 141 for generating estimated spectroscopic images based on each prepared wavelength set are arranged in the image selection region 135B. Input boxes 143 in which wavelength values of the wavelength set are inputted for generating estimated spectroscopic images are arranged in the image selection region 135C.

The operator can select any playback mode in such a manner that the operator performs movement of a pointer 145, selecting operation and inputting of numerical values through the input portion 91 (such as a mouse or a keyboard) while viewing the contents displayed on the reproducing and display portion 101. When there is an operator's instruction to switch the playback mode (S35), the recording/reproducing control portion 87 performs an image display process in accordance with the designated playback mode (S36). The switching of the playback mode can be performed at any time up to the end of the image file (S37).

<Ordinary Image Playback Mode>

Figure 10:
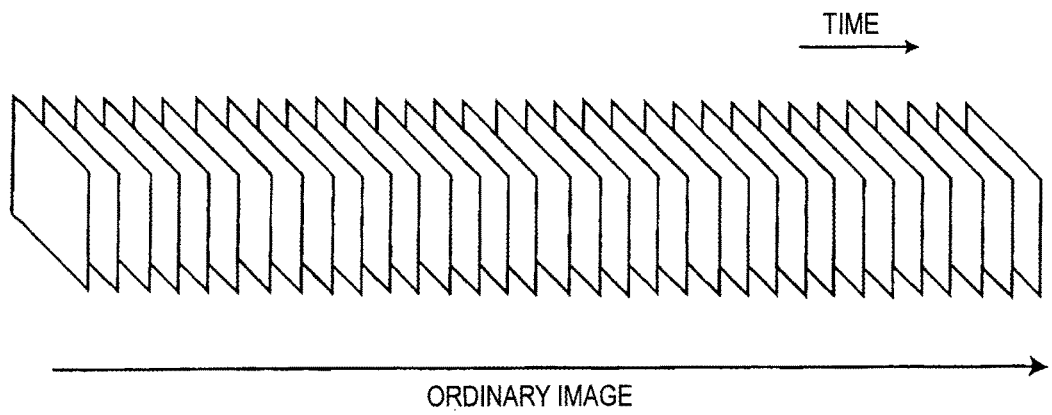
FIG. 10 is an explanatory view showing a state of image reproduction in an ordinary image playback mode.

In a mode in which ordinary images are played back and displayed, observed images stored in the image information storage portion 93 are played back on the reproducing and display portion 101. That is, as shown in FIG. 10, ordinary images as the image signal from the imaging device 27 of the endoscope 11 are always displayed continuously.

According to this mode, even when estimated spectroscopic images were observed at the time of endoscopic inspection, ordinary images of the inspection region can be confirmed so that diagnosis accuracy can be improved.

<Observation Image Playback Mode>

Figure 11:
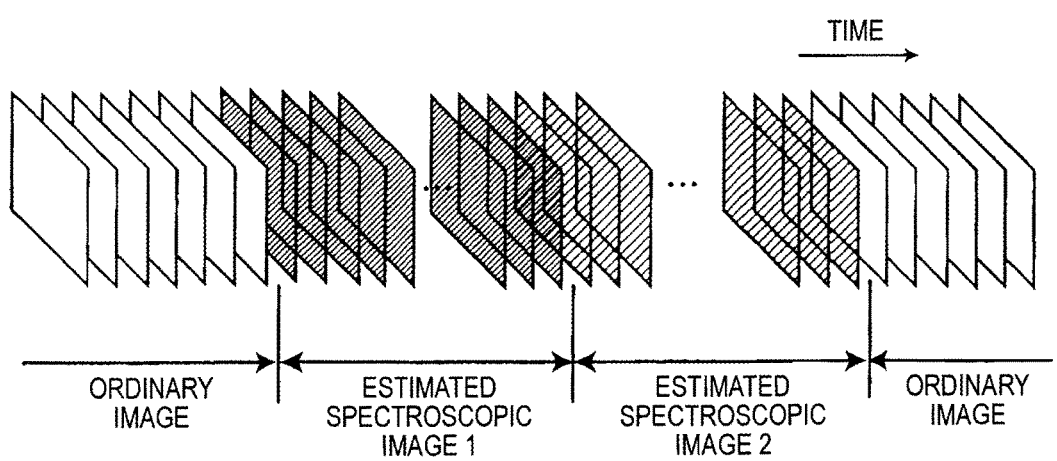
FIG. 11 is an explanatory view showing a state of image display in an observation image playback mode.

In a mode in which observed images at the time of endoscopic inspection are played back and displayed, when, for example, images were observed while image switching was executed in order of ordinary image, estimated spectroscopic image 1, estimated spectroscopic image 2 and ordinary image shown in FIG. 4, images are played back and displayed while image switching is executed in the same timing as at the time of endoscopic inspection in order of ordinary image, estimated spectroscopic image 1, estimated spectroscopic image 2 and ordinary image as shown in FIG. 11.

Figure 12:
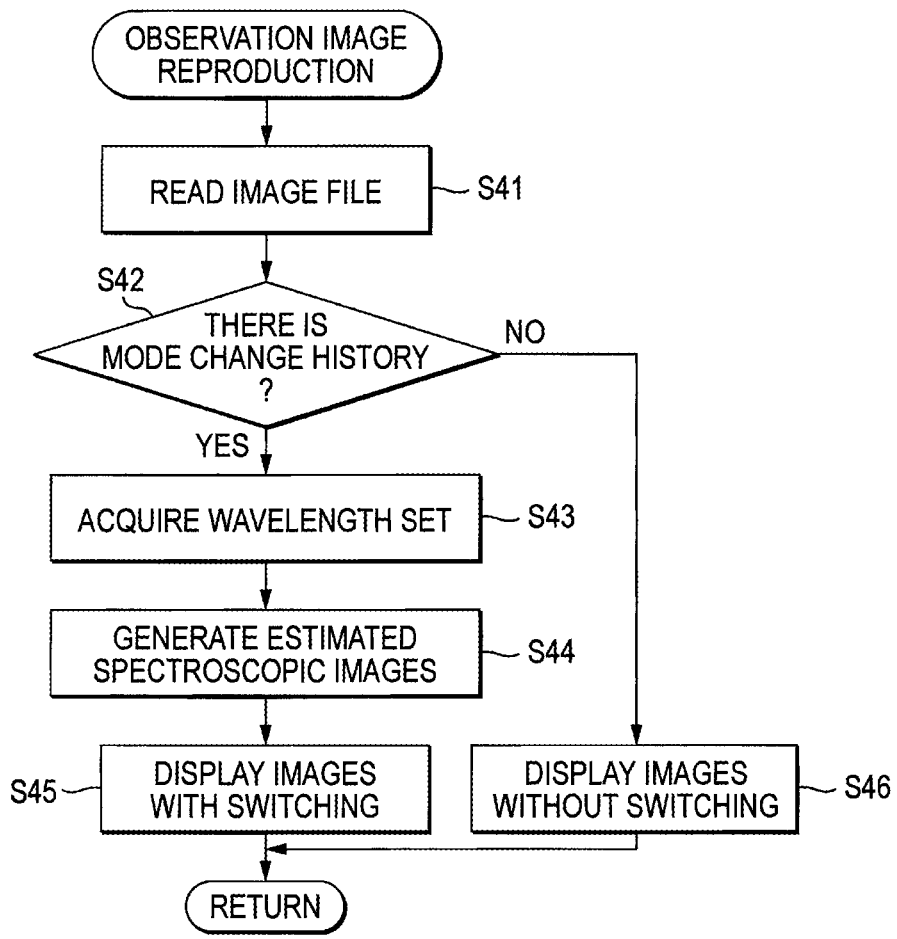
FIG. 12 is a flow chart showing a processing procedure in the observation image playback mode.

FIG. 12 shows a flow chart of the contents of the processing procedure in this case. The recording/reproducing control portion 87 (see FIG. 3) reads an image file from the storage device 99 (S41) and checks whether there is a mode change history or not, by referring to image switching timing information stored in the image-relevant information storage portion 95 by the information extraction portion 89 (S42). When there is a mode change history, wavelength set information stored in the image-relevant information storage portion 95 is acquired (S43). The feature image generating portion 97 generates estimated spectroscopic images based on the acquired wavelength set information in accordance with the image information stored in the image information storage portion 93 (S44).

The recording/reproducing control portion 87 switches the image information displayed on the reproducing and display portion 101 and displays generated estimated spectroscopic images. On the other hand, when there is no mode change history in the timing information, image display is continued without image switching.

According to this mode, the image file can be reproduced as the same motion images as those observed at the time of endoscopic inspection, so that images of an inspection region which is noticed by the endoscopic operator can be faithfully reproduced in the same state as the time of inspection. Thus, the endoscope operator's diagnosis result and medical opinion contents on the inspection region can be confirmed again easily. Even when another person than the operator interprets the endoscopic images, the operator's intension of observation can be transmitted to the person easily.

<Wavelength Set Selection Mode>

In a mode in which any wavelength set is selected to generate and display estimated spectroscopic images, any wavelength set is selected from wavelength sets registered in advance as represented by the image selection region 135B in FIG. 9, so that estimated spectroscopic images with the selected wavelength set are generated and displayed. As a specific example, the wavelength sets set in advance are wavelength sets shown in Table 2.

TABLE 2

| No. | Type | λ1, λ2, λ3 (nm) |
|---|---|---|
| CH1 | Standard Set | 400, 500, 600 |
| CH2 | Blood Vessel Set | 470, 500, 670 |
| CH3 | Blood Vessel Set | 475, 510, 685 |
| CH4 | Set for Drawing Specific Tissue | 440, 480, 520 |
| CH5 | Set for Drawing Specific Tissue | 480, 510, 580 |
| CH6 | Set for Drawing Difference between Oxyhemoglobin and Deoxyhemoglobin | 400, 430, 475 |
| CH7 | Set for Drawing Difference between Blood and Carotene | 415, 450, 500 |
| CH8 | Set for Drawing Difference between Blood and Cytoplasm | 420, 550, 600 |

When any one of the aforementioned wavelength sets is used selectively, desired feature images can be obtained easily. Desired feature images can be also obtained in accordance with the purpose of observation when the aforementioned wavelength sets are not used but wavelength values of any wavelength set for generating estimated spectroscopic images as represented by the image selection region 135C in FIG. 9 are arbitrarily inputted to the input boxes 143.

According to the medical image recording apparatus, the medical image reproducing apparatus and the medical image recording/reproducing apparatus described above, image data of motion images recorded at endoscopic inspection can be displayed as the same images as images displayed and observed at the time of endoscopic inspection, and desired spectroscopic images can be obtained in such a manner that spectroscopic arithmetic operation is normally performed on the recorded images in any timing. As a result, image information observed with image switching by the operator at the time of endoscopic inspection can be reproduced after the endoscopic inspection in the same manner as at the time of inspection, so that any person can interpret estimated spectroscopic images in the same condition as the operator made diagnosis on the affected region. Any estimated spectroscopic images can be generated in any timing regardless of the contents of the spectroscopic arithmetic operation at the time of endoscopic inspection. Accordingly, it is possible to make detailed diagnosis on the affected region based on the recorded images, so that the range of use of image diagnosis can be widened.

<Modification 1>

A modification of the medical image recording apparatus, the medical image reproducing apparatus and the medical image recording/reproducing apparatus will be described below.

Figure 13:
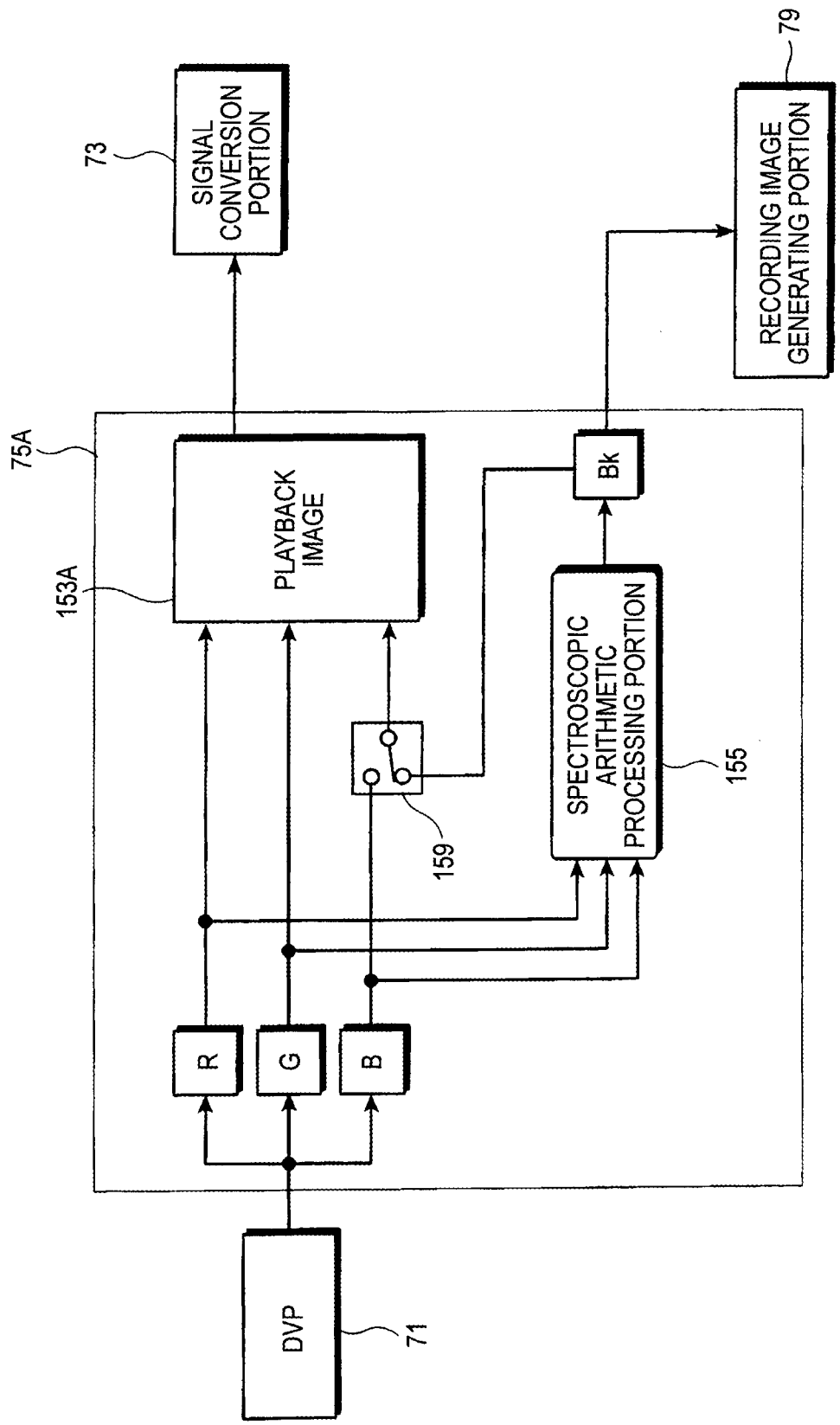
FIG. 13 is a block diagram representing Modification 1 of the image arithmetic portion shown in FIG. 1.

FIG. 13 shows a block diagram representing Modification 1 of the image arithmetic portion 75 shown in FIG. 1.

In the medical image recording apparatus 100 shown in FIG. 1, arithmetic processing of estimated spectroscopic images is performed by the color space conversion processing circuit 113 which performs matrix arithmetic operation in the image arithmetic portion 75. In this modification, in an image arithmetic portion 75A, RGB signals from the DVP 71 are bifurcated and inputted to a spectroscopic arithmetic processing portion 155 so that the spectroscopic arithmetic processing portion 155 performs spectroscopic arithmetic operation of captured images in the procedure of generation of estimated spectroscopic images in FIG. 5 to generate B-highlighted images Bk in which visible short-wavelength image components are highlighted.

The B-highlighted images Bk are designed to include image information with wavelength components of 380 nm to 450 nm, particularly image information with a visible short-wavelength band of 400 nm to 420 nm. The visible short-wavelength image information includes high intensity of information of blood capillary images of a living body tissue surface layer and microscopic patterns of a mucous membrane surface. Although the B-highlighted images Bk can be calculated by spectroscopic arithmetic processing, the B-highlighted images Bk may be calculated alternatively by a process of changing the gain of B signal to adjust the luminance value of image data.

A switch 159 is provided in the image arithmetic portion 75A to perform switching to either of the case where R, G and B components from the DVP 71 are directly used as playback images and the case where R, G and Bk components-combined images (feature images) in which R and G components are combined with the B-highlighted image Bk component generated by the spectroscopic arithmetic processing portion 155 are used as playback images. Playback images 153A of R, G and B components or R, G and Bk components in which R and G components are combined with the B-highlighted image Bk component are inputted to the signal conversion portion 73 and displayed on the display portion 15.

According to this configuration, switching to either of captured images as ordinary images and feature images in which blood capillary images of a living body tissue surface layer and microscopic patterns of a mucous membrane surface are highlighted can be made freely by the switch 159. Whenever the endoscope control portion 77 of the processor 33 receives an observation mode change button 61 pushing-down signal outputted from the scope control portion 59, the switch 159 outputs a switching signal to the image arithmetic portion 75A to perform switching.

The B-highlighted images Bk are outputted to the recording image generating portion 79. In the recording image generating portion 79, captured images from the DVP 71 are used as image information of observed images and the B-highlighted images Bk due to the image arithmetic portion 75A, timing information of the switching signal, etc. are used as image-relevant information so that the captured images and the B-highlighted images are converted into image file formats respectively. In this modification, a multi-picture format or the like is used as the image file format so that various kinds of image information are recorded for the captured images and the B-highlighted images.

The endoscope controller 13 outputs data of the image file to the image recording/reproducing portion 19 through the interface 81. The image recording/reproducing portion 19 records the inputted image file in the storage device 99 shown in FIG. 3.

Images in the image file recorded by the image recording/reproducing portion 19 as described above are played back as follows.

The recording/reproducing control portion 87 shown in FIG. 3 analyzes the image file recorded in the storage device 99 and extracts captured images as recording image information, B-highlighted images as image-relevant information and timing information as image-relevant information. The image information storage portion 93 stores the captured images. The image-relevant information storage portion 95 stores the B-highlighted images and the timing information.

The feature image generating portion 97 generates playback images by referring to the image information storage portion 93 and the image-relevant information storage portion 95 and displays the playback images in desired timing on the reproducing and display portion 101.

According to this configuration, while switching to either captured images as ordinary images as observed images or B-highlighted images in which blood capillary images of a living body tissue surface layer and microscopic patterns of a mucous membrane surface are highlighted is made freely, the switched images can be displayed on the reproducing and display portion 101. Switching to either of the two kinds of images may be made in synchronization with the aforementioned timing information or may be made in accordance with a switching instruction given through the input portion 91. According to this display switching technique, B-highlighted images are recorded directly so that responsiveness of image switching can be enhanced without image arithmetic processing at the time of image switching. Accordingly, smooth image switching operation can be made and, moreover, image switching can be performed at any time so that diagnosis accuracy at interpretation of endoscopic images is improved.

<Modification 2>

A technique of generating pattern-highlighted images with highlighted image components in a specific wavelength band and recording pattern-extracted images indicating a blood vessel position, etc. based on the pattern-highlighted images may be used as another technique than the aforementioned technique of recording B-highlighted images.

Figure 14:
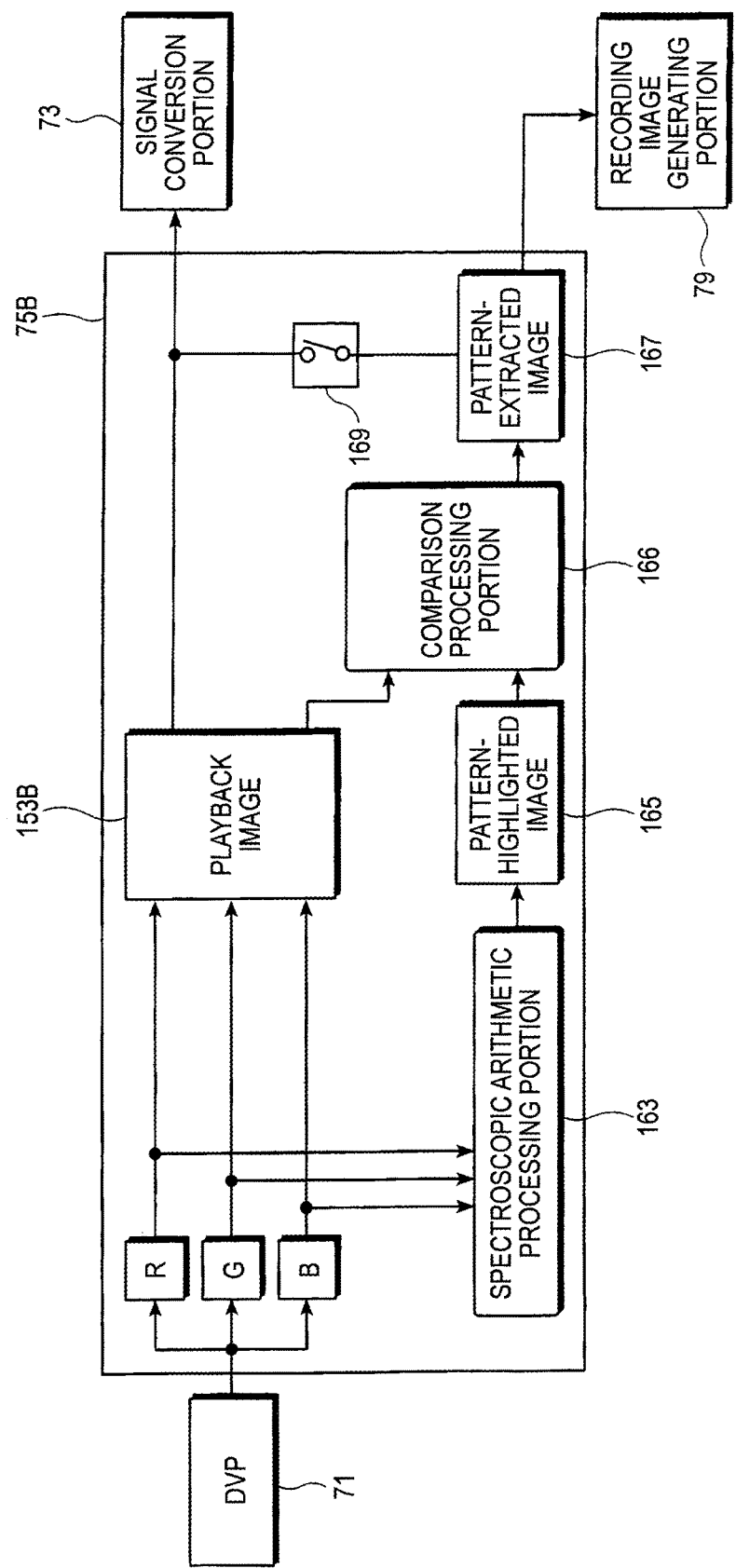
FIG. 14 is a block diagram showing Modification 2 of the image arithmetic portion shown in FIG. 1.

FIG. 14 shows a block diagram of an image arithmetic portion 75B in this case.

A spectroscopic arithmetic processing portion 163 applies spectroscopic arithmetic operation on captured images as shown in the procedure of generation of estimated spectroscopic images in FIG. 5 to generate pattern-highlighted images 165 with highlighted image components in a specific wavelength band. The pattern-highlighted images 165 are estimated spectroscopic images obtained by performing spectroscopic arithmetic processing on captured images. For example, visible short-wavelength image components may be highlighted as patterns in which blood capillary images of a living body tissue surface layer and microscopic patterns of a mucous membrane surface are particularly highlighted. Alternatively, visible long-wavelength image components may be highlighted as patterns in which blood vessel information of a mucous membrane deep part is highlighted.

A comparison processing portion 166 compares the pattern-highlighted images 165 with playback images 153B to obtain pattern-extracted images 167 in which only specific patterns such as blood capillary images, microscopic patterns and blood vessel patterns of a mucous membrane deep part are extracted. Alternatively, as to the pattern-extracted images 167, the pattern-highlighted images 165 are compared with the playback images 153B to obtain blood vessel position data and the blood vessel position data is used for obtaining images in which blood vessel images are analytically reproduced based on coordinate data or vector data of respective blood vessel images with respect to line images, so that blood vessel pattern images can be generated as feature images.

A method of obtaining blood vessel position data is as follows. First, pattern-highlighted images are compared with captured images to extract a large number of line image patterns as a blood vessel image from difference information between the pattern-highlighted image and the captured image. Coordinate values of respective blood vessels are obtained individually from the pattern extraction result. For example, this blood vessel image extraction process can be performed by first-order derivative-based edge detection such as Canny's method and removal of isolated points from an edge detected by the edge detection. Alternatively, this blood vessel pattern image may be generated by computer graphics technology using a computer apparatus mounted with a video capture board.

The pattern-extracted image 167 is combined with the playback image 153B through a changeover switch 169, so that the combined image is inputted to the signal conversion portion 73 so as to be displayed on the display portion 15. Switching to either the case where the playback image 153B is directly used as a playback image or the case where a feature image using the pattern-extracted image 167 is displayed as a display image is performed by the switch 169. The switch 169 performs switching whenever the endoscope control portion 77 of the processor 33 receives an observation mode change button 61 pushing-down signal outputted from the scope control portion 59 in the same manner as in Modification 1.

Figure 15:
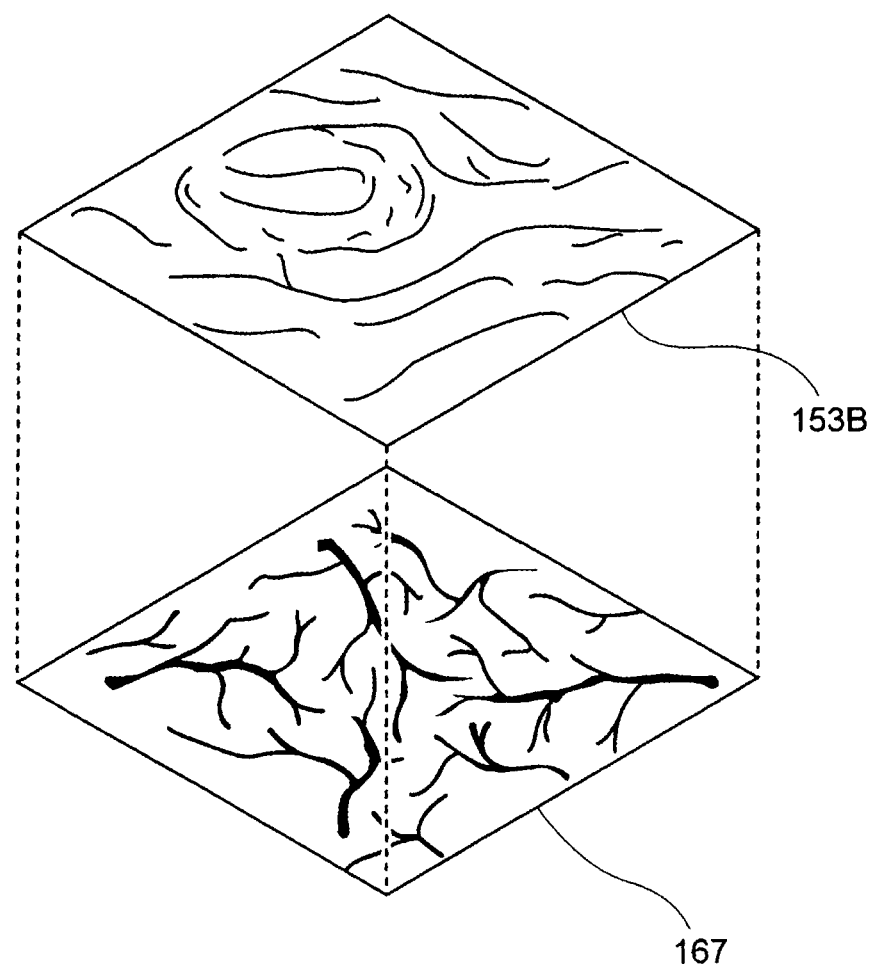
FIG. 15 is an explanatory view schematically showing a state where a captured image is combined with a blood vessel image.

FIG. 15 schematically shows a state where the playback image 153B is combined with the pattern-extracted image 167 indicating blood vessel patterns. The pattern-extracted image 167 is blood capillaries of a living body tissue surface layer and microscopic patterns of a mucous membrane surface slightly displayed with low visibility in the playback image 153B. When this pattern-extracted image 167 is reproduced as a combined image obtained by averaging the pattern-extracted image 167 and the playback image 153B, feature information can be reproduced as an image in a state where visibility is enhanced. Display of blood vessel images with another color than the actual observation color can be made easy.

Incidentally, the aforementioned pattern-extracted image 167 is outputted to the recording image generating portion 79 in the same manner as in Modification 1, converted into an image file format and recorded in the storage device 99 of the image recording/reproducing portion 19. Also in reproduction, the image displayed on the reproducing and display portion 101 can be switched in the same timing as at the time of endoscopic inspection in synchronization with the aforementioned timing information. Because the feature image generating portion 97 has a function of generating estimated spectroscopic images shown in FIG. 5, estimated spectroscopic images can be generated based on the wavelength set used for generating estimated spectroscopic images at the time of endoscopic inspection or any wavelength set inputted through the input portion 91 so that the estimated spectroscopic images can be displayed while ordinary images are switched to the estimated spectroscopic images. That is, switching to either ordinary images or various kinds of feature images displayed on the display portion 15 at the time of inspection can be made for display or both ordinary images and feature images can be displayed simultaneously.

Although the disclosed medical image recording and reproducing method is formed by hardware such as the image arithmetic portion 75, the recording image generating portion 79, the endoscope control portion 77, etc. shown in FIG. 1, the method may be implemented as software in such a manner that processes executed by the respective portions are executed by a CPU and the CPU executes a program. Alternatively, a part of processes executed by the respective portions may be formed by software. In this case, a general-purpose computer system such as a work station, a personal computer, etc. may be used. That is, a program for achieving respective processes is prepared in advance so that the method can be achieved when this program is executed by the CPU of the computer system.

The invention is not limited to the aforementioned exemplary embodiment but changes or applications made by those skilled in the art based on description in this specification and well-known technology is intended by the invention and included in the scope claimed for protection. For example, in this specification, description has been made in the case where an endoscope is used as a medical instrument. However, the same image recording/reproducing can be performed on other kinds of medical instruments such as an ultrasonic diagnosis apparatus, an X-ray diagnosis apparatus, a nuclear magnetic resonance apparatus, etc.

In addition, information of observed images recorded as an image file may be recorded as RAW data outputted by the imaging device. In this case, image data can be reproduced more faithfully.

As described above, the following items are disclosed in this specification.

(1) A medical image reproducing apparatus for reproducing image information recorded as an image file, wherein:

the image file is outputted from a medical instrument capable of switching to either observed images of a subject or images different from the observed images and displaying the switched images, and includes image information of the observed images and timing information indicating display timing of switching to the images different from the observed images and displaying the switched images, the medical image reproducing apparatus comprising:

an information extraction portion which extracts the image information and image-relevant information including the timing information from the image file;

an image arithmetic portion which generates feature images by highlighting specific features contained in the observed images by using the extracted image information and the extracted image-relevant information;

a reproducing and display portion which displays inputted display images; and an image switching control portion which switches the display image outputted to the reproducing and display portion to either the recorded image information or the feature images, the image switching control portion having a function of switching the display images in synchronization with the timing information.

With the configuration of (1), image data outputted from a medical instrument can be displayed as the same images as images observed at the time of inspection using the medical instrument.

(2) The medical image reproducing apparatus according to (1), further comprising:

an input portion which designates display images outputted to the reproducing and display portion; wherein:

the image switching control portion switches the display images in accordance with the designation through the input portion.

With the configuration of (2), desired feature images can be selected by switching and displayed in any timing in accordance with an instruction given from the input portion.

(3) The medical image reproducing apparatus according to (2), wherein:

the image-relevant information includes wavelength set information composed of wavelengths; and the image arithmetic portion generates the feature images by obtaining estimated spectroscopic images with the wavelength set set in the image-relevant information by matrix arithmetic operation of the observed images extracted from the image file.

With the configuration of (3), estimated spectroscopic images with a set of wavelengths which are set at the time of outputting the image file (at the time of inspection) can be reproduced.

(4) The medical image reproducing apparatus according to (3), wherein:

the input portion inputs any one of wavelength sets prepared in advance; and the image arithmetic portion generates the feature images by arithmetic operation of estimated spectroscopic images with the inputted wavelength set.

With the configuration of (4), because a plurality of wavelength sets are prepared in advance, an appropriate wavelength set corresponding to an observation region can be selected easily so that desired feature images can be generated.

(5) The medical image reproducing apparatus according to (3), wherein:

the input portion inputs wavelength values of the wavelength set; and the image arithmetic portion generates the feature images by arithmetic operation of estimated spectroscopic images with the inputted wavelength set.

With the configuration of (5), because wavelength values of a wavelength set are inputted directly, estimated spectroscopic images with a desired wavelength set can be obtained reliably.

(6) The medical image reproducing apparatus according to any one of (1) to (5), wherein:

the feature images are images in which spectroscopic intensity in a visible short-wavelength band of 400 nm to 420 nm is made higher than spectroscopic intensity in any other visible wavelength band.

With the configuration of (6), blood capillary images of a living body tissue surface layer or information of microscopic patterns of a mucous membrane surface can be observed clearly.

(7) The medical image reproducing apparatus according to any one of (1) to (6), wherein:

the medical instrument is an endoscope.

With the configuration of (7), because the medical instrument is an endoscope, the image file can be reproduced as the same images as images observed at the time of endoscopic inspection, so that an inspection region which attracts endoscopic operator's attention can be reproduced faithfully in the same condition as that at the time of inspection. Accordingly, a result of endoscopic operator's diagnosis on the inspection region and contents of an endoscopic operator's medical opinion can be reconfirmed easily. When another person than the operator interprets the medical images, the operator's observation intention can be transmitted easily to the person.

(8) The medical image reproducing apparatus according to any one of (1) to (7), wherein:

the image file format is a motion JPEG format.

With the configuration of (8), because motion JPEG images which are a large number of still images are used, information of observed images and image-relevant information including information as to timings when switching display was performed and image generation information for generating feature images are recorded as one image file so that these pieces of information can be reproduced from the image file. Thus, data input/output can be performed at a high speed and management of the image file is also easy.

(9) A medical image reproducing method for reproducing image information recorded as an image file, wherein:

the image file is outputted from a medical instrument capable of switching to either observed images of a subject or images different from the observed images and displaying the switched images, and includes image information of the observed images and timing information indicating timing of switching to the images different from the observed images and displaying the switched images, the medical image reproducing method comprising:

extracting the image information and image-relevant information including the timing information from the image file;

generating feature images by highlighting specific features contained in the observed images by using the extracted image information and the extracted image-relevant information; and switching display images outputted to a reproducing and display portion in synchronization with the timing information when the display images are switched to either the recorded image information or the feature images.

(10) The medical image reproducing method according to (9), further comprising:

designating display images outputted to the reproducing and display portion through an input portion to switch the display images to the designated display images.

(11) The medical image reproducing method according to (10), wherein:

estimated spectroscopic images with a wavelength set composed of wavelengths are obtained by matrix arithmetic operation of the observed images extracted from the image file to generate the feature images.

(12) The medical image reproducing method according to (11), wherein:

any one of wavelength sets prepared in advance is inputted and estimated spectroscopic images with the inputted wavelength set are obtained by arithmetic operation to generate the feature images.

(13) The medical image reproducing method according to (11), wherein:

wavelength values of the wavelength set are inputted and estimated spectroscopic images with the inputted wavelength set are obtained by arithmetic operation to generate the feature images.

(14) A non-transitory computer readable medium storing a program causing a computer to execute a process for the medical image reproducing method according to (9).

(15) A medical image recording apparatus for recording observed images of a subject outputted from a medical instrument, comprising:

an image arithmetic portion which generates feature images by highlighting specific features contained in the observed images;

a display portion which displays inputted display images;

a display image switching portion which switches the display images outputted to the display portion to either the observed images or images including the feature images generated by the image arithmetic portion; and an image information recording portion which records, as an image file, image-relevant information including timing information at execution of image switching by the display image switching portion and image generation information for generating the feature images and image information of the observed images.

With the configuration of (15), image data outputted from a medical instrument can be recorded so that the same images as images observed at the time of inspection using the medical instrument can be displayed.

(16) The medical image recording apparatus according to (15), wherein:

the image arithmetic portion obtains estimated spectroscopic images by matrix arithmetic operation of the observed images by using a wavelength set including arbitrarily set wavelengths and outputs the estimated spectroscopic images as the feature images; and the image-relevant information includes the wavelength set information as the image generation information.

With the configuration of (16), estimated spectroscopic images with a set of wavelengths which are set at the time of outputting the image file (at the time of inspection) can be reproduced.

(17) The medical image recording apparatus according to (15) or (16), wherein:

the feature images are images in which spectroscopic intensity in a visible short-wavelength band of 400 nm to 420 nm is made higher than spectroscopic intensity in any other visible wavelength band.

With the configuration of (17), blood capillary images of a living body tissue surface layer or information of microscopic patterns of a mucous membrane surface can be observed clearly.

(18) The medical image recording apparatus according to any one of (15) to (17), wherein:

the image file format is a motion JPEG format.

With the configuration of (18), because motion JPEG images which are a large number of still images are used, image information can be recorded while compressed so that the size of each image file can be reduced.

(19) The medical image recording apparatus according to (18), wherein:

the image information recording portion records the image-relevant information and image information of the observed images as one image file.

With the configuration of (19), data input/output can be performed at a high speed and management of the image file is also easy.

(20) The medical image recording apparatus according to (18) or (19), wherein:

the image recording portion records the image-relevant information in a header region of the JPEG format and the image information of the observed images in an image recording region of the JPEG format.

With the configuration of (20), image-relevant information and image information can be recorded on different regions respectively so that correspondence between the image information and the image-relevant information can be made easily.

(21) The medical image recording apparatus according to any one of (15) to (20), wherein:

the medical instrument is an endoscope.

With the configuration of (21), because the medical instrument is an endoscope, the image file can be reproduced as the same images as images observed at the time of endoscopic inspection, so that an inspection region which attracts endoscopic operator's attention can be reproduced faithfully in the same condition as that at the time of inspection. Accordingly, a result of endoscopic operator's diagnosis on the inspection region and contents of an endoscopic operator's medical opinion can be reconfirmed easily. When another person than the operator interprets the medical images, the operator's observation intention can be transmitted easily to the person.

(22) A medical image recording/reproducing apparatus comprising:

a medical image recording apparatus according to any one of (15) to (21) and an image reproducing portion which reads an image file recorded by the medical image recording apparatus, and switches to either the observed images or the feature images and displays the switched images on the reproducing and display portion in synchronization with the timing information recorded in the image file.

With the configuration of (22), image data outputted from a medical instrument can be displayed as the same images as images observed at the time of inspection using the medical instrument.

(23) The medical image recording/reproducing apparatus according to (22) further comprising:

a feature image generating portion which obtains estimated spectroscopic images with a wavelength set including arbitrarily set wavelengths by matrix arithmetic operation of the observed images read from the image file to thereby generate the feature images; wherein:

the image-relevant information includes the wavelength set information.

With the configuration of (23), estimated spectroscopic images with a set of wavelengths which are set at the time of outputting the image file (at the time of inspection) can be reproduced.

(24) A medical image recording method for recording observed images of a subject outputted from a medical instrument, comprising:

generating feature images by highlighting specific features contained in the observed images; and recording, as an image file, image-relevant information including timing information at execution of image switching and image generation information for generating the feature images and image information of the observed images when display images outputted to a display portion are switched to either the observed images or images including the feature images.

(25) The medical image recording method according to (24) wherein:

estimated spectroscopic images are obtained by matrix arithmetic operation of the observed images by using a wavelength set including arbitrarily set wavelengths so that the estimated spectroscopic images are outputted as the feature images; and the wavelength set information is included as the image generation information in the image-relevant information.

(26) A medical image recording/reproducing method comprising:

reading an image file recorded by a medical image recording method according to (24) or (25); and switching to either the observed images or the feature images and displaying the switched images on the reproducing and display portion in synchronization with the timing information recorded in the image file.

(27) The medical image recording/reproducing method according to (26), wherein:

estimated spectroscopic images with a wavelength set including arbitrarily set wavelengths are obtained by matrix arithmetic operation of the observed images read from the image file to thereby generate the feature images; and the wavelength set information is included in the image-relevant information.

(28) A non-transitory computer readable medium storing a program causing a computer to execute a process for the medical image recording method according to (24).

(29) A non-transitory computer readable medium storing a program causing a computer to execute a process for the medical image recording method according to (26).

What is claimed is:

1. A medical image reproducing apparatus for reproducing image information recorded as an image file, wherein:
the image file is output from a medical instrument capable of switching between observed images of a subject and feature images different from the observed images for display,
the image file is recorded to include:
motion image information of the observed images,
timing information indicating a history of display timing of switching between the observed images and the feature images different from the observed images for display in execution of observing the subject by the medical instrument, and
image processing condition information for generating and displaying the feature images different from the observed images,
the medical image reproducing apparatus comprising:
an information extractor which extracts the motion image information, the timing information, and the image processing condition information from the image file;
an image generator which generates the feature images by highlighting specific features contained in the observed images by using the extracted motion image information and the extracted image processing condition information;
a display which displays input images; and
an image switch controller which switches the display images output to the display to either the recorded image information or the feature images, the image controller having a function of performing the switching in synchronization with the timing information,
wherein the output displayed images are configured to be reproduced as same motion images and same feature images as images observed during the execution of observing the subject by the medical instrument by switching image processing conditions indicated in the image processing condition information in accordance with the timing information, and
wherein the feature images are images in which spectroscopic intensity in a visible short-wavelength band of 400 nm to 420 nm is made higher than spectroscopic intensity in any other visible wavelength band.

2. The medical image reproducing apparatus according to claim 1, further comprising:
an inputter which designates display images output to the display;
wherein:
the image switch controller switches the displayed images in accordance with the designation through the inputter.

3. The medical image reproducing apparatus according to claim 2, wherein:
the image processing condition information includes wavelength set information composed of wavelengths; and
the image arithmetic generator generates the feature images by obtaining estimated spectroscopic images with the wavelength set information by matrix arithmetic operation of the observed images extracted from the image file.

4. The medical image reproducing apparatus according to claim 3, wherein:
the inputter inputs any one of wavelength sets prepared in advance; and
the image arithmetic generator generates the feature images by arithmetic operation of estimated spectroscopic images with the input wavelength set.

5. The medical image reproducing apparatus according to claim 3, wherein:
the inputter inputs wavelength values of the wavelength set; and
the image arithmetic generator generates the feature images by arithmetic operation of estimated spectroscopic images with the input wavelength set.

6. The medical image reproducing apparatus according to claim 1, wherein:
the medical instrument is an endoscope.

7. The medical image reproducing apparatus according to claim 1, wherein:
the image file format is a motion JPEG format.

8. A medical image recording apparatus for recording observed images of a subject outputted from a medical instrument, comprising:
an image arithmetic generator which generates feature images by highlighting specific features contained in the observed images;
a display which displays input display images;
a display image switch controller which switches the display images output to the display portion to either the observed images or the feature images generated by the image arithmetic generator; and
an image information recorder which records an image file,
wherein the image file are recorded to include:
motion image information of the observed images,
timing information indicating a history of display timing of the switching of the display images between the observed images and the feature images in execution of observing the subject by the medical instrument, and
image processing condition information for generating and displaying the feature images,
wherein the output displayed images are configured to be reproduced as same motion images and same feature images as images observed during the execution of observing the subject by the medical instrument by switching image processing conditions indicated in the image processing condition information in accordance with the timing information,
wherein the feature images are images in which spectroscopic intensity in a visible short-wavelength band of 400 nm to 420 nm is made higher than spectroscopic intensity in any other visible wavelength band.

9. The medical image recording apparatus according to claim 8, wherein:
the image arithmetic generator obtains estimated spectroscopic images by matrix arithmetic operation of the observed images by using a wavelength set including arbitrarily set wavelengths and outputs the estimated spectroscopic images as the feature images; and
the image processing condition information includes the wavelength set information as the image processing condition information.

10. The medical image recording apparatus according to claim 8, wherein:
the image file format is a motion JPEG format.

11. The medical image recording apparatus according to claim 10, wherein:
the image information recorder records the motion image information of the observed images, the timing information and the image processing condition information as one image file.

12. The medical image recording apparatus according to claim 10, wherein:
the image recording recorder records the timing information and the image processing condition information in a header region of the motion JPEG format and the motion image information of the observed images in an image recording region of the motion JPEG format.

13. The medical image recording apparatus according to claim 8, wherein:
the medical instrument is an endoscope.

14. A medical image recording/reproducing apparatus comprising:
a medical image recording apparatus according to claim 8; and
an image reproducer which reads an image file recorded by the medical image recording apparatus, and switches to either the observed images or the feature images and displays the switched images on the reproducing and display portion in synchronization with the timing information recorded in the image file.

15. The medical image recording/reproducing apparatus according to claim 14, further comprising:
a feature image generator which obtains estimated spectroscopic images with a wavelength set including arbitrarily set wavelengths by matrix arithmetic operation of the observed images read from the image file to thereby generate the feature images; wherein:
the image processing condition information includes the wavelength set information.

16. A medical image recording apparatus for recording observed images of a subject outputted from a medical instrument, comprising:
an image arithmetic generator which generates feature images by highlighting specific features contained in the observed images;
a display which displays input display images;
a display image switch controller which switches the display images output to the display portion to either the observed images or the feature images generated by the image arithmetic generator; and
an image information recorder which records an image file,
wherein the image file are recorded to include:
motion image information of the observed images,
timing information indicating a history of display timing of the switching of the display images between the observed images and the feature images in execution of observing the subject by the medical instrument, and
image processing condition information for generating and displaying the feature images,
wherein the output displayed images are configured to be reproduced as same motion images and same feature images as images observed during the execution of observing the subject by the medical instrument by switching image processing conditions indicated in the image processing condition information in accordance with the timing information,
the image file format is a motion JPEG format, and the image information recorder records the motion image information of the observed images, the timing information and the image processing condition information as one image file.

17. The medical image recording apparatus according to claim 16, wherein:
the image arithmetic generator obtains estimated spectroscopic images by matrix arithmetic operation of the observed images by using a wavelength set including arbitrarily set wavelengths and outputs the estimated spectroscopic images as the feature images; and
the image processing condition information includes the wavelength set information as the image processing condition information.

18. The medical image recording apparatus according to claim 16, wherein:
the image recording recorder records the timing information and the image processing condition information in a header region of the motion JPEG format and the motion image information of the observed images in an image recording region of the motion JPEG format.

19. The medical image recording apparatus according to claim 16, wherein:
the medical instrument is an endoscope.

20. A medical image recording/reproducing apparatus comprising:
a medical image recording apparatus according to claim 16; and
an image reproducer which reads an image file recorded by the medical image recording apparatus, and switches to either the observed images or the feature images and displays the switched images on the reproducing and display portion in synchronization with the timing information recorded in the image file.

21. The medical image recording/reproducing apparatus according to claim 20, further comprising:
a feature image generator which obtains estimated spectroscopic images with a wavelength set including arbitrarily set wavelengths by matrix arithmetic operation of the observed images read from the image file to thereby generate the feature images; wherein:
the image processing condition information includes the wavelength set information.

* * * * *